(12) United States Patent
Gates et al.

(10) Patent No.: US 9,519,861 B1
(45) Date of Patent: Dec. 13, 2016

(54) GENERATING DIGITAL MODELS OF NUTRIENTS AVAILABLE TO A CROP OVER THE COURSE OF THE CROP'S DEVELOPMENT BASED ON WEATHER AND SOIL DATA

(71) Applicant: THE CLIMATE CORPORATION, San Francisco, CA (US)

(72) Inventors: John Gates, San Francisco, CA (US); Steven De Gryze, San Francisco, CA (US)

(73) Assignee: The Climate Corporation, San Francisco, CA (US)

( * ) Notice: Subject to any disclaimer, the term of this patent is extended or adjusted under 35 U.S.C. 154(b) by 0 days.

(21) Appl. No.: 14/842,321

(22) Filed: Sep. 1, 2015

Related U.S. Application Data

(60) Provisional application No. 62/192,754, filed on Jul. 15, 2015.

(51) Int. Cl.
*G06N 5/02* (2006.01)
*G06F 17/50* (2006.01)

(52) U.S. Cl.
CPC .............. *G06N 5/02* (2013.01); *G06F 17/5022* (2013.01)

(58) Field of Classification Search
None
See application file for complete search history.

(56) References Cited

U.S. PATENT DOCUMENTS

| | | | |
|---|---|---|---|
| 5,668,719 A | 9/1997 | Bobrov et al. | |
| 6,874,707 B2 * | 4/2005 | Skinner | A01G 17/02 239/542 |

(Continued)

FOREIGN PATENT DOCUMENTS

EP 2 196 085 A2 6/2010

OTHER PUBLICATIONS

Ahmad, Sajjad, Ajay Kalra, and Haroon Stephen. "Estimating soil moisture using remote sensing data: A machine learning approach." Advances in Water Resources 33.1 (2010): 69-80.*
Ines, Amor VM, and Peter Droogers. "Inverse modelling in estimating soil hydraulic functions: A genetic algorithm approach." Hydrology and Earth System Sciences Discussions 6.1 (2002): 49-66.*
Van Arkel, Zach, and Amy L. Kaleita. "Identifying sampling locations for field- scale soil moisture estimation using K- means clustering." Water Resources Research 50.8 (2014): 7050-7057.*

(Continued)

*Primary Examiner* — Kakali Chaki
*Assistant Examiner* — Daniel Pellett
(74) *Attorney, Agent, or Firm* — Hickman Palermo Becker Bingham LLP; Elliot H. Karlin

(57) ABSTRACT

A system for generating digital models of nitrogen availability based on field data, weather forecast data, and models of water flow, temperature, and crop uptake of nitrogen and water is provided. In an embodiment, field data and forecast data are received by an agricultural intelligence computing system. Based on the received data, the agricultural intelligence computing system models changes in temperature of different soil layers, moisture content of different soil layers, and loss of nitrogen and water to the soil through crop uptake, leaching, denitrification, volatilization, and evapotranspiration. The agricultural intelligence computing system creates a digital model of nitrogen availability based on the temperature, moisture content, and loss models. The agricultural intelligence computing system may then send nitrogen availability data to a field manager computing device and/or use the nitrogen availability data to create notifications, recommendations, agronomic models, and/or control parameters for an application controller.

28 Claims, 9 Drawing Sheets

(56) References Cited

U.S. PATENT DOCUMENTS

| | | | |
|---|---|---|---|
| 7,171,912 B2* | 2/2007 | Fraisse | A01B 49/06 111/118 |
| 9,107,341 B2* | 8/2015 | Martinez | G05D 11/138 |
| 2006/0254371 A1* | 11/2006 | Shiloni | E02D 1/06 73/864.34 |
| 2007/0039745 A1* | 2/2007 | Anderson | A01B 79/005 172/6 |
| 2007/0260400 A1* | 11/2007 | Morag | G06Q 10/00 702/1 |
| 2010/0024296 A1* | 2/2010 | Lazarus | G06Q 50/02 47/58.1 SC |
| 2010/0332039 A1* | 12/2010 | Danieli | A01C 21/007 700/284 |
| 2012/0083907 A1 | 4/2012 | Motavalli et al. | |
| 2012/0101861 A1* | 4/2012 | Lindores | G06Q 10/06 705/7.11 |
| 2012/0109614 A1* | 5/2012 | Lindores | A01B 79/005 703/11 |
| 2013/0144827 A1* | 6/2013 | Trevino | G06N 5/02 706/46 |
| 2013/0332205 A1* | 12/2013 | Friedberg | G06Q 40/08 705/4 |
| 2014/0012732 A1* | 1/2014 | Lindores | A01B 79/005 705/37 |
| 2014/0067745 A1* | 3/2014 | Avey | G06N 5/02 706/46 |
| 2014/0165713 A1* | 6/2014 | Frey | G01N 33/24 73/64.56 |
| 2015/0254800 A1* | 9/2015 | Johnson | C05C 11/00 382/141 |

OTHER PUBLICATIONS

Sattari, S. Z., et al. "Crop yield response to soil fertility and N, P, K inputs in different environments: testing and improving the QUEFTS model." Field Crops Research 157 (2014): 35-46.*

Granlund, Kirsti, et al. "Estimation of the impact of fertilisation rate on nitrate leaching in Finland using a mathematical simulation model." Agriculture, ecosystems & environment 80.1 (2000): 1-13.*

Negm, L. M., et al. "DRAINMOD—DSSAT model for simulating hydrology, soil carbon and nitrogen dynamics, and crop growth for drained crop land." Agricultural Water Management 137 (2014): 30-45.*

Taylor, DL. "Innovation in the fields" The Salinas Californian: Oct. 19, 2013.*

European Patent Office, Search Report in application No. PCT/US2016/029385, dated Jul. 28, 2016, 12 pages.

European Claims in application No. PCT/US2016/029385, dated Jul. 2016, 11 pages.

* cited by examiner (a)

(b)

GENERATING DIGITAL MODELS OF NUTRIENTS AVAILABLE TO A CROP OVER THE COURSE OF THE CROP'S DEVELOPMENT BASED ON WEATHER AND SOIL DATA

BENEFIT CLAIM AND CROSS-REFERENCE TO RELATED APPLICATIONS

This application claims the benefit under 35 U.S.C. §119 (e) of provisional application 62/192,754, filed Jul. 15, 2015, the entire disclosure of which is hereby incorporated by reference for all purposes as if fully set forth herein. This application is related to provisional application 62/049,898, filed Sep. 12, 2014; provisional application 62/049,937, filed Sep. 12, 2014; provisional application 62/049,909, filed Sep. 12, 2014; and provisional application 62/049,929, filed Sep. 12, 2014, the entire disclosures of which are hereby incorporated by reference for all purposes as if fully set forth herein.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright or rights whatsoever. © 2015 The Climate Corporation.

FIELD OF THE DISCLOSURE

The present disclosure relates to digital computer modeling of nutrients in a field, such as nitrogen, phosphorus, and potassium, using weather data, soil data, and crop management data received over a network. Additionally, the present disclosure relates to computer generation of notifications, recommendations, and graphical user interfaces based on digital models of nutrient availability.

BACKGROUND

The approaches described in this section are approaches that could be pursued, but not necessarily approaches that have been previously conceived or pursued. Therefore, unless otherwise indicated, it should not be assumed that any of the approaches described in this section qualify as prior art merely by virtue of their inclusion in this section.

Nutrients are essential in the growth and development of crops. Crops absorb nutrients such as nitrogen, phosphorus, and potassium in the surrounding soil to facilitate crop growth. Different types of crops have different requirements for each nutrient. When a crop is unable to meet its nutrient needs, the crop suffers. For example, a lack of nitrogen may lead to destruction of a crop's leaves. Additionally, once the nitrogen concentration in a plant decreases below a critical threshold, photosynthesis and dry matter accumulation is negatively impacted. An end result is that the yield of a crop which does not receive enough nutrients is decreased.

While nutrients in the soil are important to plant growth, it is difficult to determine when soil lacks one or more nutrients without performing nutrient tests. Additionally, the impact of a specific nutrient application is not readily apparent. For example, an application of forty pounds per acre of nitrogen at one time may result in a net increase of ten pounds of nitrogen per acre available to a crop due to nitrogen loss through a variety of factors and low transmission rates to the crop. The same application of forty pounds per acre of nitrogen at another time may result in the majority of the applied nitrogen being available to a crop. Without an understanding of all of the factors that affect whether a crop will receive the nitrogen added to a field, nitrogen application tends to be relatively blind. A farmer may apply nitrogen to a field at specific stages in a crop's development or when the crop appears to be suffering from a lack of nitrogen. Such applications of nitrogen are inefficient as they either involve wasting nitrogen or not adding enough nitrogen to satisfy the needs of a plant. Additionally, nitrogen lost to the field through leaching may create environmental problems when the nitrogen joins the watershed.

The amount of each nutrient available to a crop tends to be dependent on a wide variety of factors. For example, moisture content, soil type, and soil temperature affect the flow of nitrogen through the soil, the lateral transmission of nitrogen to the roots of a plant, and the loss of nitrogen through denitrification, volatilization, and leaching. Additionally, the uptake of nutrients by a crop varies from crop to crop and varies based on the stage of development of a specific crop. Furthermore, different layers of soil have may have different compositions, different temperatures, and different moisture contents. Thus, the transmission of nutrients through the soil may vary from soil layer to soil layer.

There is a need for a system which receives data about a particular field, ranging from soil data to weather data, and models the availability of nutrients in the particular field based on the received data. A few difficulties arise in the context of modeling nutrient availability based on the wide variety of factors. A first difficulty in modeling nutrient availability is determining nutrient availability in the future, such that intelligent nutrient application decisions can be made before problems begin to arise. While current soil samples may be used to determine nutrient availability at a given time, nutrient availability in the future is difficult to model without future temperature and precipitation data. A second difficulty in modeling nutrient availability is the computation expense of modeling factors that affect nutrient availability. For example, methods of modeling moisture content in soil tend to be extremely computationally expensive, requiring an iterative scheme to solve a non-linear differential equation, or computational inexpensive but extremely inaccurate.

SUMMARY OF THE DISCLOSURE

The appended claims may serve as a summary of the disclosure.

DETAILED DESCRIPTION

Figure 1:
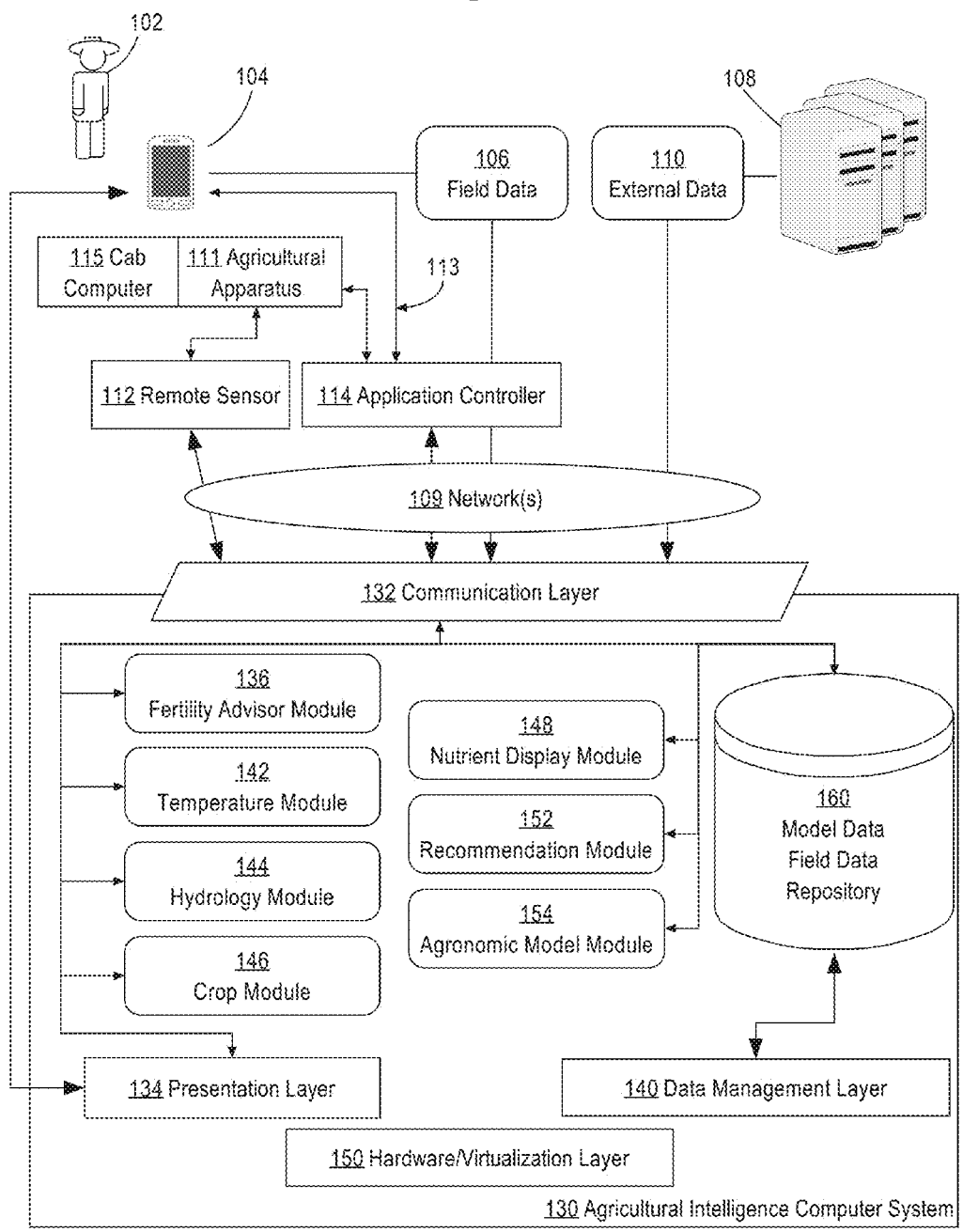
FIG. 1 illustrates an example computer system that is configured to perform the functions described herein, shown in a field environment with other apparatus with which the system may interoperate.

In the following description, for the purposes of explanation, numerous specific details are set forth in order to provide a thorough understanding of the present disclosure. It will be apparent, however, that embodiments may be practiced without these specific details. In other instances, well-known structures and devices are shown in block diagram form in order to avoid unnecessarily obscuring the present disclosure. Embodiments are disclosed in sections according to the following outline:
1. GENERAL OVERVIEW
2. EXAMPLE AGRICULTURAL INTELLIGENCE COMPUTER SYSTEM
    2.1. STRUCTURAL OVERVIEW
    2.2. APPLICATION PROGRAM OVERVIEW
    2.3. DATA INGEST TO THE COMPUTER SYSTEM
    2.4. PROCESS OVERVIEW—AGRONOMIC MODEL TRAINING
    2.5. IMPLEMENTATION EXAMPLE—HARDWARE OVERVIEW
3. FERTILITY ADVISOR
    3.1. RECEIVED DATA
    3.2. NUTRIENT AVAILABILITY MODEL
        3.2.1. INITIAL NUTRIENT AVAILABILITY
        3.2.2. NUTRIENT GAINS AND LOSSES
    3.3. TEMPERATURE MODEL
    3.4. HYDROLOGY MODEL
        3.4.1. ADAPTIVE TIME STEPS
        3.4.2. PARAMETERIZATION
    3.5. CROP MODEL
4. DATA USAGE
    4.1. NUTRIENT AVAILABILITY GRAPHS
    4.2. AGRONOMIC MODELS
    4.3. RECOMMENDATIONS
    4.4. NOTIFICATIONS
    4.5. USER DEFINED PROPOSALS
5. BENEFITS OF CERTAIN EMBODIMENTS
6. EXTENSIONS AND ALTERNATIVES 1. General Overview Aspects of the disclosure generally relate to computer-implemented techniques for generating nutrient availability models and transmitting nutrient availability data to a computing device. In an embodiment, an agricultural intelligence computing system is programmed or configured to receive, over a network, field data from a field manager computing device and external data, such as soil data and weather predictions, from an external server computing device. A temperature module of the agricultural intelligence computing system models changes in temperature of each soil layer on a field based, at least in part, on soil factors, moisture content, and estimated solar radiation. A hydrology module of the agricultural intelligence computing system models changes in moisture content of each layer of soil on a field based, at least in part, on soil factors, temperature models, and estimated precipitation. A crop module of the agricultural intelligence computing system models an uptake of nitrogen and water by a crop on the field based, at least in part, on estimated moisture content, estimated temperature, soil factors, crop factors, and nitrogen availability factors. Based on the modeled data and data received over the network, a fertility advisor module creates a digital model of nutrient availability for the crop on the field. The agricultural intelligence computing system may then generate alerts, recommendations, agronomic models, and/or nutrient availability displays and send them to the field manager computing device.

In an embodiment, a method comprises: receiving over a network at an agricultural intelligence computing system comprising one or more processors and digital memory, electronic digital data comprising a plurality of values representing crop data, soil data, and weather data for one or more fields; using digitally programmed logic in a temperature module of the agricultural intelligence computing system, creating and storing in computer memory a first digital model of temperature of soil in the one or more fields based, at least in part, on the plurality of values representing crop data, soil data, and weather data; using digitally programmed logic in a hydrology module of the agricultural intelligence computing system, creating and storing in the computer memory a second digital model of water flow through the one or more fields based, at least in part, on the plurality of values representing crop data, soil data, and weather data; using digitally programmed logic in a crop module of the agricultural intelligence computing system, creating and storing a third digital model of an uptake of water of one or more crops on the one or more fields based, at least in part, on the second digital model of water flow through the one or more fields and the plurality of values representing crop data, soil data, and weather data; using digitally programmed logic in the crop module of the agricultural intelligence computing system, creating and storing a fourth digital model of an uptake of a nutrient of the one or more crops on the one or more fields based, at least in part, on the plurality of values representing crop data, soil data, and weather data; using digitally programmed logic in a fertility advisor module of the agricultural intelligence computing system, creating and displaying a fifth digital model of nutrient availability in the one or more fields based, at least in part on the first digital model of temperature of soil, the second digital model of water flow, the third digital model of the uptake of water of the one or more crops, the fourth digital model of the uptake of the nutrient of the one or more crops, and the plurality of values representing crop data, soil data, and weather data for the one or more fields.

Other features and aspect of the disclosure will become apparent in the drawings, description, and claims.

2. Example Agricultural Intelligence Computer System 2.1 Structural Overview

FIG. 1 illustrates an example computer system that is configured to perform the functions described herein, shown in a field environment with other apparatus with which the system may interoperate. In one embodiment, a user 102 owns, operates, or possesses a field manager computing device 104 in a field location or associated with a field location such as a field intended for agricultural activities or a management location for one or more agricultural fields. The field manager computing device 104 is programmed or configured to provide field data 106 to an agricultural intelligence computer system 130 via one or more networks 109.

Examples of field data 106 include (a) identification data (for example, acreage, field name, field identifiers, geographic identifiers, boundary identifiers, crop identifiers, and any other suitable data that may be used to identify farm land, such as a common land unit (CLU), lot and block number, a parcel number, geographic coordinates and boundaries, Farm Serial Number (FSN), farm number, tract number, field number, section, township, and/or range), (b) harvest data (for example, crop type, crop variety, crop rotation, whether the crop is grown organically, harvest date, Actual Production History (APH), expected yield, yield, crop price, crop revenue, grain moisture, tillage practice, and previous growing season information), (c) soil data (for example, type, composition, pH, organic matter (OM), cation exchange capacity (CEC)), (d) planting data (for example, planting date, seed(s) type, relative maturity (RM) of planted seed(s), seed population), (e) fertilizer data (for example, nutrient type (Nitrogen, Phosphorous, Potassium), application type, application date, amount, source), (f) pesticide data (for example, pesticide, herbicide, fungicide, other substance or mixture of substances intended for use as a plant regulator, defoliant, or desiccant), (g) irrigation data (for example, application date, amount, source), (h) weather data (for example, precipitation, temperature, wind, forecast, pressure, visibility, clouds, heat index, dew point, humidity, snow depth, air quality, sunrise, sunset), (i) imagery data (for example, imagery and light spectrum information from an agricultural apparatus sensor, camera, computer, smartphone, tablet, unmanned aerial vehicle, planes or satellite), (j) scouting observations (photos, videos, free form notes, voice recordings, voice transcriptions, weather conditions (temperature, precipitation (current and over time), soil moisture, crop growth stage, wind velocity, relative humidity, dew point, black layer)), and (k) soil, seed, crop phenology, pest and disease reporting, and predictions sources and databases.

An external data server computer 108 is communicatively coupled to agricultural intelligence computer system 130 and is programmed or configured to send external data 110 to agricultural intelligence computer system 130 via the network(s) 109. The external data server computer 108 may be owned or operated by the same legal person or entity as the agricultural intelligence computer system 130, or by a different person or entity such as a government agency, non-governmental organization (NGO), and/or a private data service provider. Examples of external data include weather data, imagery data, soil data, or statistical data relating to crop yields, among others. External data 110 may consist of the same type of information as field data 106. In some embodiments, the external data 110 is provided by an external data server 108 owned by the same entity that owns and/or operates the agricultural intelligence computer system 130. For example, the agricultural intelligence computer system 130 may include a data server focused exclusively on a type of that might otherwise be obtained from third party sources, such as weather data.

An agricultural apparatus 111 has one or more remote sensors 112 fixed thereon, which sensors are communicatively coupled either directly or indirectly via agricultural apparatus 111 to the agricultural intelligence computer system 130 and are programmed or configured to send sensor data to agricultural intelligence computer system 130. Examples of agricultural apparatus 111 include tractors, combines, harvesters, planters, trucks, fertilizer equipment, unmanned aerial vehicles, and any other item of physical machinery or hardware, typically mobile machinery, and which may be used in tasks associated with agriculture. In some embodiments, a single unit of apparatus 111 may comprise a plurality of sensors 112 that are coupled locally in a network on the apparatus; controller area network (CAN) is an example of such a network that can be installed in combines or harvesters. Application controller 114 is communicatively coupled to agricultural intelligence computer system 130 via the network(s) 109 and is programmed or configured to receive one or more scripts to control an operating parameter of an agricultural vehicle or implement from the agricultural intelligence computer system 130. For instance, a controller area network (CAN) bus interface may be used to enable communications from the agricultural intelligence computer system 130 to the agricultural apparatus 111, such as how the CLIMATE FIELDVIEW DRIVE, available from The Climate Corporation, San Francisco, Calif., is used. Sensor data may consist of the same type of information as field data 106.

The apparatus 111 may comprise a cab computer 115 that is programmed with a cab application, which may comprise a version or variant of the mobile application for device 104 that is further described in other sections herein. In an embodiment, cab computer 115 comprises a compact computer, often a tablet-sized computer or smartphone, with a color graphical screen display that is mounted within an operator's cab of the apparatus 111. Cab computer 115 may implement some or all of the operations and functions that are described further herein for the mobile computer device 104.

The network(s) 109 broadly represent any combination of one or more data communication networks including local area networks, wide area networks, internetworks or internets, using any of wireline or wireless links, including terrestrial or satellite links. The network(s) may be implemented by any medium or mechanism that provides for the exchange of data between the various elements of FIG. 1. The various elements of FIG. 1 may also have direct (wired or wireless) communications links. The sensors 112, controller 114, external data server computer 108, and other elements of the system each comprise an interface compatible with the network(s) 109 and are programmed or configured to use standardized protocols for communication across the networks such as TCP/IP, CAN protocol and higher-layer protocols such as HTTP, TLS, and the like.

Agricultural intelligence computer system 130 is programmed or configured to receive field data 106 from field manager computing device 104, external data 110 from external data server computer 108, and sensor data from remote sensor 112. Agricultural intelligence computer system 130 may be further configured to host, use or execute one or more computer programs, other software elements, digitally programmed logic such as FPGAs or ASICs, or any combination thereof to perform translation and storage of data values, construction of digital models of one or more crops on one or more fields, generation of recommendations and notifications, and generation and sending of scripts to application controller 114, in the manner described further in other sections of this disclosure.

In an embodiment, agricultural intelligence computer system 130 is programmed with or comprises a communication layer 132, presentation layer 134, data management layer 140, hardware/virtualization layer 150, and model and field data repository 160. "Layer," in this context, refers to any combination of electronic digital interface circuits, microcontrollers, firmware such as drivers, and/or computer programs or other software elements.

Communication layer 132 may be programmed or configured to perform input/output interfacing functions including sending requests to field manager computing device 104, external data server computer 108, and remote sensor 112 for field data, external data, and sensor data respectively. Communication layer 132 may be programmed or configured to send the received data to model and field data repository 160 to be stored as field data 106.

Presentation layer 134 may be programmed or configured to generate a graphical user interface (GUI) to be displayed on field manager computing device 104, cab computer 115 or other computers that are coupled to the system 130 through the network 109. The GUI may comprise controls for inputting data to be sent to agricultural intelligence computer system 130, generating requests for models and/or recommendations, and/or displaying recommendations, notifications, models, and other field data.

Data management layer 140 may be programmed or configured to manage read operations and write operations involving the repository 160 and other functional elements of the system, including queries and result sets communicated between the functional elements of the system and the repository. Examples of data management layer 140 include JDBC, SQL server interface code, and/or HADOOP interface code, among others. Repository 160 may comprise a database. As used herein, the term "database" may refer to either a body of data, a relational database management system (RDBMS), or to both. As used herein, a database may comprise any collection of data including hierarchical databases, relational databases, flat file databases, object-relational databases, object oriented databases, and any other structured collection of records or data that is stored in a computer system. Examples of RDBMS's include, but are not limited to including, ORACLE®, MYSQL, IBM® DB2, MICROSOFT® SQL SERVER, SYBASE®, and POSTGRESQL databases. However, any database may be used that enables the systems and methods described herein.

When field data 106 is not provided directly to the agricultural intelligence computer system via one or more agricultural machines or agricultural machine devices that interacts with the agricultural intelligence computer system, the user 102 may be prompted via one or more user interfaces on the user device (served by the agricultural intelligence computer system) to input such information. In an example embodiment, the user 102 may specify identification data by accessing a map on the user device (served by the agricultural intelligence computer system) and selecting specific CLUs that have been graphically shown on the map. In an alternative embodiment, the user 102 may specify identification data by accessing a map on the user device (served by the agricultural intelligence computer system 130) and drawing boundaries of the field over the map. Such CLU selection or map drawings represent geographic identifiers. In alternative embodiments, the user 102 may specify identification data by accessing field identification data (provided as shape files or in a similar format) from the U. S. Department of Agriculture Farm Service Agency or other source via the user device and providing such field identification data to the agricultural intelligence computer system.

In an embodiment, model and field data is stored in model and field data repository 160. Model data comprises data models created for one or more fields. For example, a crop model may include a digitally constructed model of the development of a crop on the one or more fields. "Model," in this context, refers to an electronic digitally stored set of executable instructions and data values, associated with one another, which are capable of receiving and responding to a programmatic or other digital call, invocation, or request for resolution based upon specified input values, to yield one or more stored output values that can serve as the basis of computer-implemented recommendations, output data displays, or machine control, among other things. Persons of skill in the field find it convenient to express models using mathematical equations, but that form of expression does not confine the models disclosed herein to abstract concepts; instead, each model herein has a practical application in a computer in the form of stored executable instructions and data that implement the model using the computer. The model data may include a model of past events on the one or more fields, a model of the current status of the one or more fields, and/or a model of predicted events on the one or more fields. Model and field data may be stored in data structures in memory, rows in a database table, in flat files or spreadsheets, or other forms of stored digital data.

In one embodiment, each of the fertility advisor module 136, temperature module 142, hydrology module 144, crop module 146, nutrient display module 148, recommendation module 152, and agronomic model module 154 comprises a set of one or more pages of main memory, such as RAM, in the agricultural intelligence computer system 130 into which executable instructions have been loaded and which when executed cause the agricultural intelligence computing system to perform the functions or operations that are described herein with reference to those modules. For example, the fertility advisor module 136 may comprise a set of pages in RAM that contain instructions which when executed cause performing the fertility advisor functions that are described herein. The instructions may be in machine executable code in the instruction set of a CPU and may have been compiled based upon source code written in JAVA, C, C++, OBJECTIVE-C, or any other human-readable programming language or environment, alone or in combination with scripts in JAVASCRIPT, other scripting languages and other programming source text. The term "pages" is intended to refer broadly to any region within main memory and the specific terminology used in a system may vary depending on the memory architecture or processor architecture. In another embodiment, each of the fertility advisor module 136, temperature module 142, hydrology module 144, crop module 146, nutrient display module 148, recommendation module 152, and agronomic model module 154 also may represent one or more files or projects of source code that are digitally stored in a mass storage device such as non-volatile RAM or disk storage, in the agricultural intelligence computer system 130 or a separate repository system, which when compiled or interpreted cause generating executable instructions which when executed cause the agricultural intelligence computing system to perform the functions or operations that are described herein with reference to those modules. In other words, the drawing figure may represent the manner in which programmers or software developers organize and arrange source code for later compilation into an executable, or interpretation into bytecode or the equivalent, for execution by the agricultural intelligence computer system 130. The executable instructions in memory, or the stored source code, specified in this paragraph are examples of "modules" as that term is used in this disclosure.

Fertility advisor module 136 is generally configured or programmed to perform translation and storage of data values, construction of digital models of one or more crops on one or more fields, construction of digital models of external effects on the one or more crops or the one or more fields, and construction of one or more digital models of availability of nutrients in the one or more fields for the one or more crops. Temperature module 142 is programmed or configured to model changes to temperature of the one or more fields based, at least in part, on data values representing weather conditions over the one or more fields. Hydrology module 144 is programmed or configured to construct one or more digital models of the flow of water above and below the surface of the one or more fields. Crop module 146 is programmed or configured to construct one or more digital models of an uptake of water and an uptake of nutrients of the one or more crops on the one or more fields. Nutrient display module 148 is programmed or configured to construct one or more nutrient availability graphs based, at least in part, on the construction of the one or more digital models of availability of nutrients in the one or more fields for the one or more crops. Recommendation module 152 is programmed or configured to create one or more recommendations for nutrient application, water application, or future tillage methods, based on the one or more digital models of availability of nutrients in the one or more fields for the one or more crops.

In an embodiment, agronomic model module 154 is programmed or configured to perform calculation and storage of agronomic factors using field data 106, external data 110, and data received from fertility advisor module 136. Agronomic model module may be configured to generate alerts based on the stored agronomic factors and send the alerts to presentation layer 134 or communication layer 132.

Figure 4:
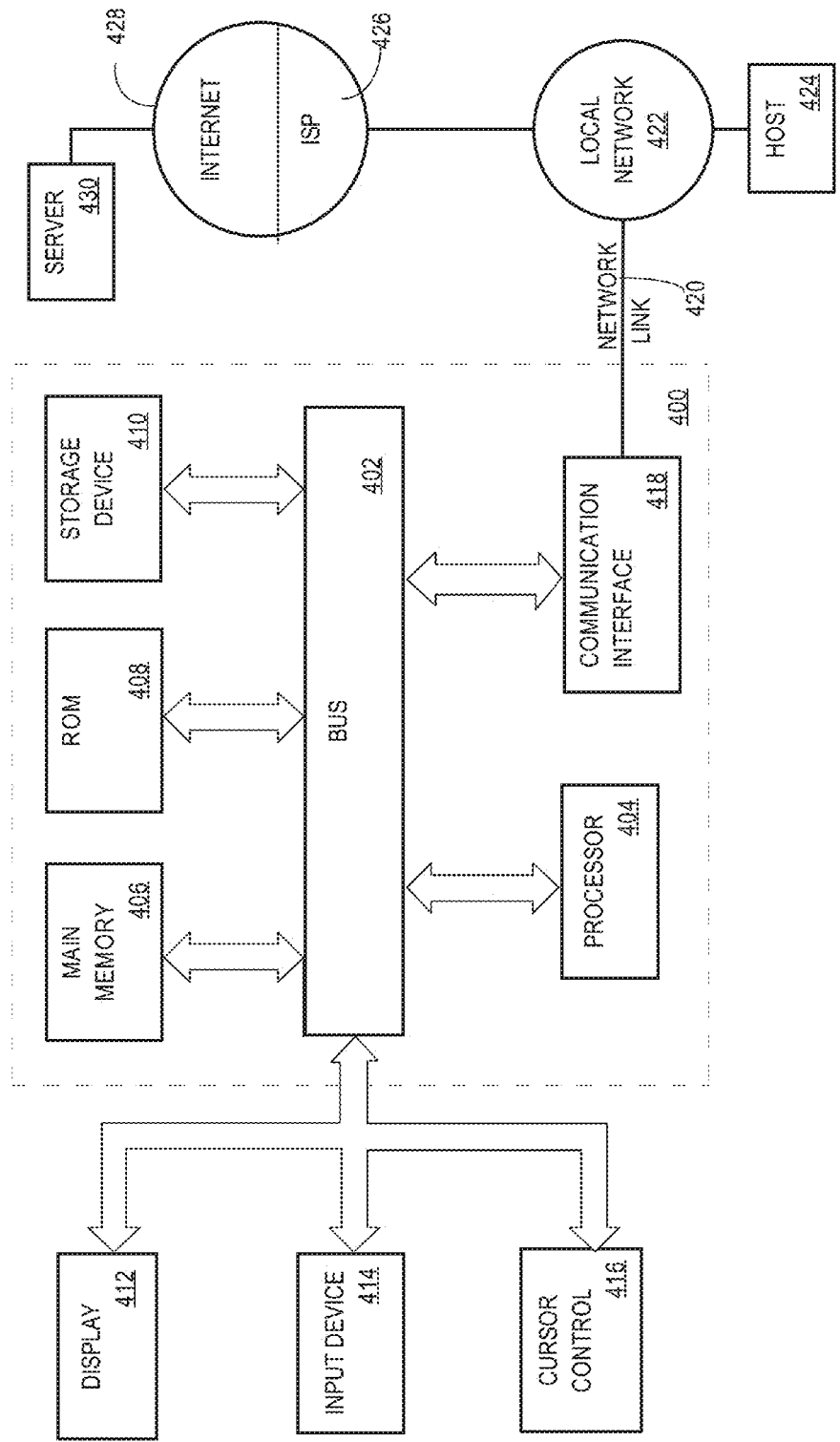
FIG. 4 is a block diagram that illustrates a computer system upon which embodiments may be implemented.

Hardware/virtualization layer 150 comprises one or more central processing units (CPUs), memory controllers, and other devices, components, or elements of a computer system such as volatile or non-volatile memory, non-volatile storage such as disk, and I/O devices or interfaces as illustrated and described, for example, in connection with FIG. 4. The layer 150 also may comprise programmed instructions that are configured to support virtualization, containerization, or other technologies.

For purposes of illustrating a clear example, FIG. 1 shows a limited number of instances of certain functional elements. However, in other embodiments, there may be any number of such elements. For example, embodiments may use thousands or millions of different mobile computing devices 104 associated with different users. Further, the system 130 and/or external data server computer 108 may be implemented using two or more processors, cores, clusters, or instances of physical machines or virtual machines, configured in a discrete location or co-located with other elements in a datacenter, shared computing facility or cloud computing facility.

2.2. Application Program Overview

In an embodiment, the implementation of the functions described herein using one or more computer programs or other software elements that are loaded into and executed using one or more general-purpose computers will cause the general-purpose computers to be configured as a particular machine or as a computer that is specially adapted to perform the functions described herein. Further, each of the flow diagrams that are described further herein may serve, alone or in combination with the descriptions of processes and functions in prose herein, as algorithms, plans or directions that may be used to program a computer or logic to implement the functions that are described. In other words, all the prose text herein, and all the drawing figures, together are intended to provide disclosure of algorithms, plans or directions that are sufficient to permit a skilled person to program a computer to perform the functions that are described herein, in combination with the skill and knowledge of such a person given the level of skill that is appropriate for inventions and disclosures of this type.

In an embodiment, user 102 interacts with agricultural intelligence computer system 130 using field manager computing device 104 configured with an operating system and one or more application programs or apps; the field manager computing device 104 also may interoperate with the agricultural intelligence computer system 130 independently and automatically under program control or logical control and direct user interaction is not always required. Field manager computing device 104 broadly represents one or more of a smart phone, PDA, tablet computing device, laptop computer, desktop computer, workstation, or any other computing device capable of transmitting and receiving information and performing the functions described herein. Field manager computing device 104 may communicate via a network using a mobile application stored on field manager computing device 104, and in some embodiments, the device may be coupled using a cable 113 or connector to the sensor 112 and/or controller 114. A particular user 102 may own, operate or possess and use, in connection with system 130, more than one field manager computing device 104 at a time.

The mobile application may provide server-side functionality, via the network 109 to one or more mobile computing devices. In an example embodiment, field manager computing device 104 may access the mobile application via a web browser or a local client application or app. Field manager computing device 104 may transmit data to, and receive data from, one or more front-end servers, using web-based protocols or formats such as HTTP, XML and/or JSON, or app-specific protocols. In an example embodiment, the data may take the form of requests and user information input, such as field data, into the mobile computing device. In some embodiments, the mobile application interacts with location tracking hardware and software on field manager computing device 104 which determines the location of field manager computing device 104 using standard tracking techniques such as multilateration of radio signals, the global positioning system (GPS), WiFi positioning systems, or other methods of mobile positioning. In some cases, location data or other data associated with the device 104, user 102, and/or user account(s) may be obtained by queries to an operating system of the device or by requesting an app on the device to obtain data from the operating system.

In an embodiment, field manager computing device 104 sends field data 106 to agricultural intelligence computer system 130 comprising or including data values representing one or more of: a geographical location of the one or more fields, tillage information for the one or more fields, crops planted in the one or more fields, and soil data extracted from the one or more fields. Field manager computing device 104 may send field data 106 in response to user input from user 102 specifying the data values for the one or more fields. Additionally, field manager computing device 104 may automatically send field data 106 when one or more of the data values becomes available to field manager computing device 104. For example, field manager computing device 104 may be communicatively coupled to remote sensor 112 and/or application controller 114. In response to receiving data indicating that application controller 114 released water onto the one or more fields, field manager computing device 104 may send field data 106 to agricultural intelligence computer system 130 indicating that water was released on the one or more fields. Field data 106 identified in this disclosure may be input and communicated using electronic digital data that is communicated between computing devices using parameterized URLs over HTTP, or another suitable communication or messaging protocol.

A commercial example of the mobile application is CLIMATE FIELDVIEW, commercially available from The Climate Corporation, San Francisco, Calif. The CLIMATE FIELDVIEW application, or other applications, may be modified, extended, or adapted to include features, functions, and programming that have not been disclosed earlier than the filing date of this disclosure. In one embodiment, the mobile application comprises an integrated software platform that allows a grower to make fact-based decisions for their operation because it combines historical data about the grower's fields with any other data that the grower wishes to compare. The combinations and comparisons may be performed in real time and are based upon scientific models that provide potential scenarios to permit the grower to make better, more informed decisions.

Figure 2:
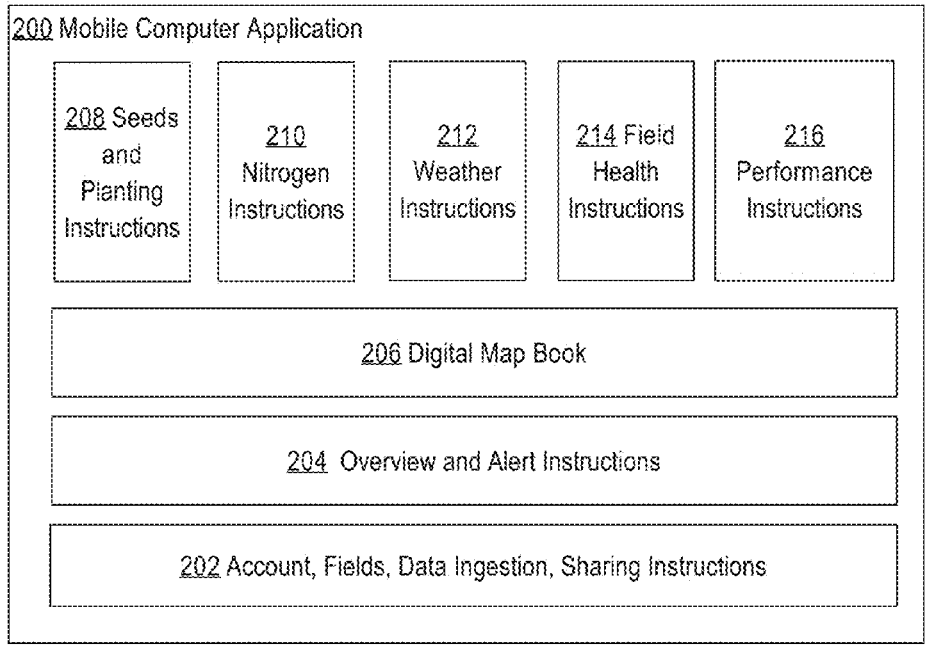
FIG. 2 illustrates two views of an example logical organization of sets of instructions in main memory when an example mobile application is loaded for execution.
Figure 2:
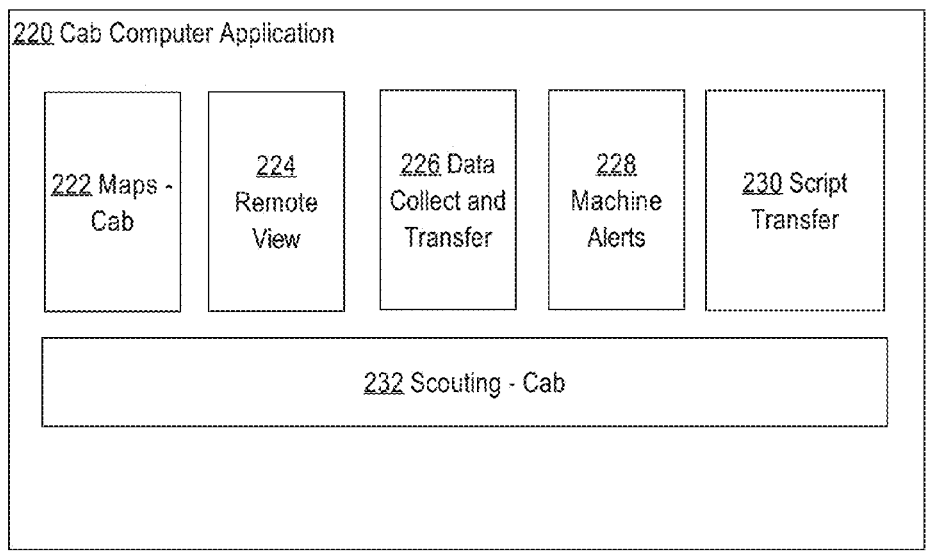

FIG. 2 illustrates two views of an example logical organization of sets of instructions in main memory when an example mobile application is loaded for execution. In FIG. 2, each named element represents a region of one or more pages of RAM or other main memory, or one or more blocks of disk storage or other non-volatile storage, and the programmed instructions within those regions. In one embodiment, in view (a), a mobile computer application 200 comprises account-fields-data ingestion-sharing instructions 202, overview and alert instructions 204, digital map book instructions 206, seeds and planting instructions 208, nitrogen instructions 210, weather instructions 212, field health instructions 214, and performance instructions 216.

In one embodiment, a mobile computer application 200 comprises account-fields-data ingestion-sharing instructions 202 are programmed to receive, translate, and ingest field data from third party systems via manual upload or APIs. Data types may include field boundaries, yield maps, as-planted maps, soil test results, as-applied maps, and/or management zones, among others. Data formats may include shape files, native data formats of third parties, and/or farm management information system (FMIS) exports, among others. Receiving data may occur via manual upload, external APIs that push data to the mobile application, or instructions that call APIs of external systems to pull data into the mobile application.

In one embodiment, digital map book instructions 206 comprise field map data layers stored in device memory and are programmed with data visualization tools and geospatial field notes. This provides growers with convenient information close at hand for reference, logging and visual insights into field performance. In one embodiment, overview and alert instructions 204 and programmed to provide an operation-wide view of what is important to the grower, and timely recommendations to take action or focus on particular issues. This permits the grower to focus time on what needs attention, to save time and preserve yield throughout the season. In one embodiment, seeds and planting instructions 208 are programmed to provide tools for seed selection, hybrid placement, and script creation, including variable rate (VR) script creation, based upon scientific models and empirical data. This enables growers to maximize yield or return on investment through optimized seed purchase, placement and population.

In one embodiment, nitrogen instructions 210 are programmed to provide tools to inform nitrogen decisions by visualizing the availability of nitrogen to crops and to create variable rate (VR) fertility scripts. This enables growers to maximize yield or return on investment through optimized nitrogen application during the season. Example programmed functions include displaying images such as SSURGO images to enable drawing of application zones; upload of existing grower-defined zones; providing an application graph to enable tuning nitrogen applications across multiple zones; output of scripts to drive machinery; tools for mass data entry and adjustment; and/or maps for data visualization, among others. "Mass data entry," in this context, may mean entering data once and then applying the same data to multiple fields that have been defined in the system; example data may include nitrogen application data that is the same for many fields of the same grower. For example, nitrogen instructions 210 may be programmed to accept definitions of nitrogen planting and practices programs and to accept user input specifying to apply those programs across multiple fields. "Nitrogen planting programs," in this context, refers to a stored, named set of data that associates: a name, color code or other identifier, one or more dates of application, types of material or product for each of the dates and amounts, method of application or incorporation such as injected or knifed in, and/or amounts or rates of application for each of the dates, crop or hybrid that is the subject of the application, among others. "Nitrogen practices programs," in this context, refers to a stored, named set of data that associates: a practices name; a previous crop; a tillage system; a date of primarily tillage; one or more previous tillage systems that were used; one or more indicators of manure application that were used. Nitrogen instructions 210 also may be programmed to generate and cause displaying a nitrogen graph, once a program is applied to a field, which indicates projections of plant use of the specified nitrogen and whether a surplus or shortfall is predicted; in some embodiments, different color indicators may signal a magnitude of surplus or magnitude of shortfall. In one embodiment, a nitrogen graph comprises a graphical display in a computer display device comprising a plurality of rows, each row associated with and identifying a field; data specifying what crop is planted in the field, the field size, the field location, and a graphic representation of the field perimeter; in each row, a timeline by month with graphic indicators specifying each nitrogen application and amount at points correlated to month names; and numeric and/or colored indicators of surplus or shortfall, in which color indicates magnitude.

In one embodiment, weather instructions 212 are programmed to provide field-specific recent weather data and forecasted weather information. This enables growers to save time and have an efficient integrated display with respect to daily operational decisions.

In one embodiment, field health instructions 214 are programmed to provide timely remote sensing images highlighting in-season crop variation and potential concerns. Example programmed functions include cloud checking, to identify possible clouds or cloud shadows; determining nitrogen indices based on field images; graphical visualization of scouting layers, including, for example, those related to field health, and viewing and/or sharing of scouting notes; and/or downloading satellite images from multiple sources and prioritizing the images for the grower, among others.

In one embodiment, performance instructions 216 are programmed to provide reports, analysis, and insight tools using on-farm data for evaluation, insights and decisions. This enables the grower to seek improved outcomes for the next year through fact-based conclusions about why return on investment was at prior levels, and insight into yieldlimiting factors. The performance instructions 216 may be programmed to communicate via the network(s) 109 to back-end analytics programs executed at external data server computer 108 and configured to analyze metrics such as yield, hybrid, population, SSURGO, soil tests, or elevation, among others. Programmed reports and analysis may include yield variability analysis, benchmarking of yield and other metrics against other growers based on anonymized data collected from many growers, or data for seeds and planting, among others.

Applications having instructions configured in this way may be implemented for different computing device platforms while retaining the same general user interface appearance. For example, the mobile application may be programmed for execution on tablets, smartphones, or server computers that are accessed using browsers at client computers. Further, the mobile application as configured for tablet computers or smartphones may provide a full app experience or a cab app experience that is suitable for the display and processing capabilities of cab computer 115. For example, referring now to view (b) of FIG. 2, in one embodiment a cab computer application 220 may comprise maps-cab instructions 222, remote view instructions 224, data collect and transfer instructions 226, machine alerts instructions 228, script transfer instructions 230, and scouting-cab instructions 232. The code base for the instructions of view (b) may be the same as for view (a) and executables implementing the code may be programmed to detect the type of platform on which they are executing and to expose, through a graphical user interface, only those functions that are appropriate to a cab platform or full platform. This approach enables the system to recognize the distinctly different user experience that is appropriate for an in-cab environment and the different technology environment of the cab. The maps-cab instructions 222 may be programmed to provide map views of fields, farms or regions that are useful in directing machine operation. The remote view instructions 224 may be programmed to turn on, manage, and provide views of machine activity in real-time or near real-time to other computing devices connected to the system 130 via wireless networks, wired connectors or adapters, and the like. The data collect and transfer instructions 226 may be programmed to turn on, manage, and provide transfer of data collected at machine sensors and controllers to the system 130 via wireless networks, wired connectors or adapters, and the like. The machine alerts instructions 228 may be programmed to detect issues with operations of the machine or tools that are associated with the cab and generate operator alerts. The script transfer instructions 230 may be configured to transfer in scripts of instructions that are configured to direct machine operations or the collection of data. The scouting-cab instructions 232 may be programmed to display location-based alerts and information received from the system 130 based on the location of the agricultural apparatus 111 or sensors 112 in the field and ingest, manage, and provide transfer of location-based scouting observations to the system 130 based on the location of the agricultural apparatus 111 or sensors 112 in the field.

2.3. Data Ingest to the Computer System

In an embodiment, external data server computer 108 stores external data 110, including soil data representing soil composition for the one or more fields and weather data representing temperature and precipitation on the one or more fields. The weather data may include past and present weather data as well as forecasts for future weather data. In an embodiment, external data server computer 108 comprises a plurality of servers hosted by different entities. For example, a first server may contain soil composition data while a second server may include weather data. Additionally, soil composition data may be stored in multiple servers. For example, one server may store data representing percentage of sand, silt, and clay in the soil while a second server may store data representing percentage of organic matter (OM) in the soil.

In an embodiment, remote sensor 112 comprises one or more sensors that are programmed or configured to produce one or more observations. Remote sensor 112 may be aerial sensors, such as satellites, vehicle sensors, planting equipment sensors, tillage sensors, fertilizer or insecticide application sensors, harvester sensors, and any other implement capable of receiving data from the one or more fields. In an embodiment, application controller 114 is programmed or configured to receive instructions from agricultural intelligence computer system 130. Application controller 114 may also be programmed or configured to control an operating parameter of an agricultural vehicle or implement. For example, an application controller may be programmed or configured to control an operating parameter of a vehicle, such as a tractor, planting equipment, tillage equipment, fertilizer or insecticide equipment, harvester equipment, or other farm implements such as a water valve. Other embodiments may use any combination of sensors and controllers, of which the following are merely selected examples.

The system 130 may obtain or ingest data under user 102 control, on a mass basis from a large number of growers who have contributed data to a shared database system. This form of obtaining data may be termed "manual data ingest" as one or more user-controlled computer operations are requested or triggered to obtain data for use by the system 130. As an example, the NITROGEN ADVISOR, commercially available from The Climate Corporation, San Francisco, Calif., may be operated to export data to system 130 for storing in the repository 160.

For example, seed monitor systems can both control planter apparatus components and obtain planting data, including signals from seed sensors via a signal harness that comprises a CAN backbone and point-to-point connections for registration and/or diagnostics. Seed monitor systems can be programmed or configured to display seed spacing, population and other information to the user via the cab computer 115 or other devices within the system 130. Examples are disclosed in U.S. Pat. No. 8,738,243 and US Pat. Pub. 20150094916, and the present disclosure assumes knowledge of those other patent disclosures.

Likewise, yield monitor systems may contain yield sensors for harvester apparatus that send yield measurement data to the cab computer 115 or other devices within the system 130. Yield monitor systems may utilize one or more remote sensors 112 to obtain grain moisture measurements in a combine or other harvester and transmit these measurements to the user via the cab computer 115 or other devices within the system 130.

In an embodiment, examples of sensors 112 that may be used with any moving vehicle or apparatus of the type described elsewhere herein include kinematic sensors and position sensors. Kinematic sensors may comprise any of speed sensors such as radar or wheel speed sensors, accelerometers, or gyros. Position sensors may comprise GPS receivers or transceivers, or WiFi-based position or mapping apps that are programmed to determine location based upon nearby WiFi hotspots, among others.

In an embodiment, examples of sensors 112 that may be used with tractors or other moving vehicles include engine speed sensors, fuel consumption sensors, area counters or distance counters that interact with GPS or radar signals, PTO (power take-off) speed sensors, tractor hydraulics sensors configured to detect hydraulics parameters such as pressure or flow, and/or and hydraulic pump speed, wheel speed sensors or wheel slippage sensors. In an embodiment, examples of controllers 114 that may be used with tractors include hydraulic directional controllers, pressure controllers, and/or flow controllers; hydraulic pump speed controllers; speed controllers or governors; hitch position controllers; or wheel position controllers provide automatic steering.

In an embodiment, examples of sensors 112 that may be used with seed planting equipment such as planters, drills, or air seeders include seed sensors, which may be optical, electromagnetic, or impact sensors; downforce sensors such as load pins, load cells, pressure sensors; soil property sensors such as reflectivity sensors, moisture sensors, electrical conductivity sensors, optical residue sensors, or temperature sensors; component operating criteria sensors such as planting depth sensors, downforce cylinder pressure sensors, seed disc speed sensors, seed drive motor encoders, seed conveyor system speed sensors, or vacuum level sensors; or pesticide application sensors such as optical or other electromagnetic sensors, or impact sensors. In an embodiment, examples of controllers 114 that may be used with such seed planting equipment include: toolbar fold controllers, such as controllers for valves associated with hydraulic cylinders; downforce controllers, such as controllers for valves associated with pneumatic cylinders, airbags, or hydraulic cylinders, and programmed for applying downforce to individual row units or an entire planter frame; planting depth controllers, such as linear actuators; metering controllers, such as electric seed meter drive motors, hydraulic seed meter drive motors, or swath control clutches; hybrid selection controllers, such as seed meter drive motors, or other actuators programmed for selectively allowing or preventing seed or an air-seed mixture from delivering seed to or from seed meters or central bulk hoppers; metering controllers, such as electric seed meter drive motors, or hydraulic seed meter drive motors; seed conveyor system controllers, such as controllers for a belt seed delivery conveyor motor; marker controllers, such as a controller for a pneumatic or hydraulic actuator; or pesticide application rate controllers, such as metering drive controllers, orifice size or position controllers.

In an embodiment, examples of sensors 112 that may be used with tillage equipment include position sensors for tools such as shanks or discs; tool position sensors for such tools that are configured to detect depth, gang angle, or lateral spacing; downforce sensors; or draft force sensors. In an embodiment, examples of controllers 114 that may be used with tillage equipment include downforce controllers or tool position controllers, such as controllers configured to control tool depth, gang angle, or lateral spacing.

In an embodiment, examples of sensors 112 that may be used in relation to apparatus for applying fertilizer, insecticide, fungicide and the like, such as on-planter starter fertilizer systems, subsoil fertilizer applicators, or fertilizer sprayers, include: fluid system criteria sensors, such as flow sensors or pressure sensors; sensors indicating which spray head valves or fluid line valves are open; sensors associated with tanks, such as fill level sensors; sectional or system-wide supply line sensors, or row-specific supply line sensors; or kinematic sensors such as accelerometers disposed on sprayer booms. In an embodiment, examples of controllers 114 that may be used with such apparatus include pump speed controllers; valve controllers that are programmed to control pressure, flow, direction, PWM and the like; or position actuators, such as for boom height, subsoiler depth, or boom position.

In an embodiment, examples of sensors 112 that may be used with harvesters include yield monitors, such as impact plate strain gauges or position sensors, capacitive flow sensors, load sensors, weight sensors, or torque sensors associated with elevators or augers, or optical or other electromagnetic grain height sensors; grain moisture sensors, such as capacitive sensors; grain loss sensors, including impact, optical, or capacitive sensors; header operating criteria sensors such as header height, header type, deck plate gap, feeder speed, and reel speed sensors; separator operating criteria sensors, such as concave clearance, rotor speed, shoe clearance, or chaffer clearance sensors; auger sensors for position, operation, or speed; or engine speed sensors. In an embodiment, examples of controllers 114 that may be used with harvesters include header operating criteria controllers for elements such as header height, header type, deck plate gap, feeder speed, or reel speed; separator operating criteria controllers for features such as concave clearance, rotor speed, shoe clearance, or chaffer clearance; or controllers for auger position, operation, or speed.

In an embodiment, examples of sensors 112 that may be used with grain carts include weight sensors, or sensors for auger position, operation, or speed. In an embodiment, examples of controllers 114 that may be used with grain carts include controllers for auger position, operation, or speed.

In an embodiment, examples of sensors 112 and controllers 114 may be installed in unmanned aerial vehicle (UAV) apparatus or "drones." Such sensors may include cameras with detectors effective for any range of the electromagnetic spectrum including visible light, infrared, ultraviolet, near-infrared (NIR), and the like; accelerometers; altimeters; temperature sensors; humidity sensors; pitot tube sensors or other airspeed or wind velocity sensors; battery life sensors; or radar emitters and reflected radar energy detection apparatus. Such controllers may include guidance or motor control apparatus, control surface controllers, camera controllers, or controllers programmed to turn on, operate, obtain data from, manage and configure any of the foregoing sensors. Examples are disclosed in U.S. patent application Ser. No. 14/831,165 and the present disclosure assumes knowledge of that other patent disclosure.

In an embodiment, sensors 112 and controllers 114 may be affixed to soil sampling and measurement apparatus that is configured or programmed to sample soil and perform soil chemistry tests, soil moisture tests, and other tests pertaining to soil. For example, the apparatus disclosed in U.S. Pat. No. 8,767,194 and U.S. Pat. No. 8,712,148 may be used, and the present disclosure assumes knowledge of those patent disclosures.

2.4 Process Overview—Agronomic Model Training

In an embodiment, the agricultural intelligence computer system 130 is programmed or configured to create an agronomic model. In this context, an agronomic model is a data structure in memory of the agricultural intelligence computer system 130 that comprises field data 106, such as identification data and harvest data for one or more fields. The agronomic model may also comprise calculated agronomic properties which describe either conditions which may affect the growth of one or more crops on a field, or properties of the one or more crops, or both. Additionally, an agronomic model may comprise recommendations based on agronomic factors such as crop recommendations, irrigation recommendations, planting recommendations, and harvesting recommendations. The agronomic factors may also be used to estimate one or more crop related results, such as agronomic yield. The agronomic yield of a crop is an estimate of quantity of the crop that is produced, or in some examples the revenue or profit obtained from the produced crop.

In an embodiment, the agricultural intelligence computer system 130 may use a preconfigured agronomic model to calculate agronomic properties related to currently received location and crop information for one or more fields. The preconfigured agronomic model is based upon previously processed field data, including but not limited to, identification data, harvest data, fertilizer data, and weather data. The preconfigured agronomic model may have been cross validated to ensure accuracy of the model. Cross validation may include comparison to ground truthing that compares predicted results with actual results on a field, such as a comparison of precipitation estimate with a rain gauge at the same location or an estimate of nitrogen content with a soil sample measurement.

Figure 3:
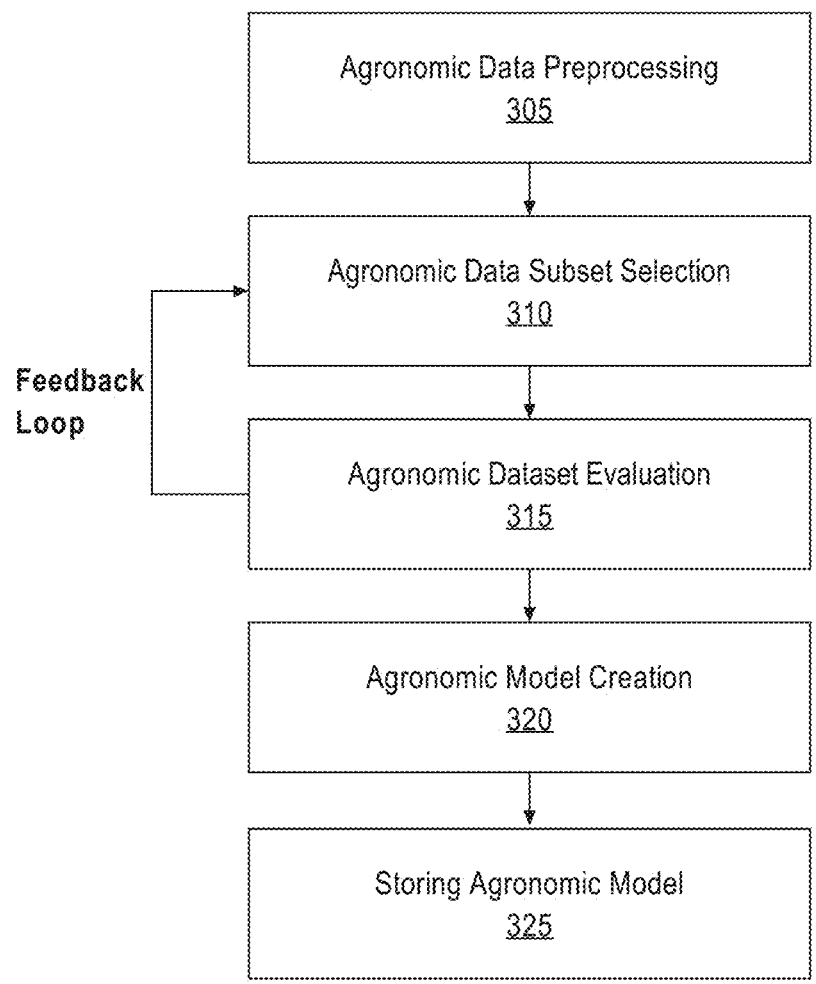
FIG. 3 illustrates a programmed process by which the agricultural intelligence computer system generates one or more preconfigured agronomic models using agronomic data provided by one or more external data sources.

FIG. 3 illustrates a programmed process by which the agricultural intelligence computer system generates one or more preconfigured agronomic models using field data provided by one or more external data sources. FIG. 3 may serve as an algorithm or instructions for programming the functional elements of the agricultural intelligence computer system 130 to perform the operations that are now described.

At block 305, the agricultural intelligence computer system 130 is configured or programmed to implement agronomic data preprocessing of field data received from one or more external data resources. The field data received from one or more external data resources may be preprocessed for the purpose of removing noise and distorting effects within the agronomic data including measured outliers that would bias received field data values. Embodiments of agronomic data preprocessing may include, but are not limited to, removing data values commonly associated with outlier data values, specific measured data points that are known to unnecessarily skew other data values, data smoothing techniques used to remove or reduce additive or multiplicative effects from noise, and other filtering or data derivation techniques used to provide clear distinctions between positive and negative data inputs.

At block 310, the agricultural intelligence computer system 130 is configured or programmed to perform data subset selection using the preprocessed field data in order to identify datasets useful for initial agronomic model generation. The agricultural intelligence computer system 130 may implement data subset selection techniques including, but not limited to, a genetic algorithm method, an all subset models method, a sequential search method, a stepwise regression method, a particle swarm optimization method, and an ant colony optimization method. For example, a genetic algorithm selection technique uses an adaptive heuristic search algorithm, based on evolutionary principles of natural selection and genetics, to determine and evaluate datasets within the preprocessed agronomic data.

At block 315, the agricultural intelligence computer system 130 is configured or programmed to implement field dataset evaluation. In an embodiment, a specific field dataset is evaluated by creating an agronomic model and using specific quality thresholds for the created agronomic model. Agronomic models may be compared using cross validation techniques including, but not limited to, root mean square error of leave-one-out cross validation (RMSECV), mean absolute error, and mean percentage error. For example, RMSECV can cross validate agronomic models by comparing predicted agronomic property values created by the agronomic model against historical agronomic property values collected and analyzed. In an embodiment, the agronomic dataset evaluation logic is used as a feedback loop where agronomic datasets that do not meet configured quality thresholds are used during future data subset selection steps (block 310).

At block 320, the agricultural intelligence computer system 130 is configured or programmed to implement agronomic model creation based upon the cross validated agronomic datasets. In an embodiment, agronomic model creation may implement multivariate regression techniques to create preconfigured agronomic data models.

At block 325, the agricultural intelligence computer system 130 is configured or programmed to store the preconfigured agronomic data models for future field data evaluation.

2.5 Implementation Example—Hardware Overview

According to one embodiment, the techniques described herein are implemented by one or more special-purpose computing devices. The special-purpose computing devices may be hard-wired to perform the techniques, or may include digital electronic devices such as one or more application-specific integrated circuits (ASICs) or field programmable gate arrays (FPGAs) that are persistently programmed to perform the techniques, or may include one or more general purpose hardware processors programmed to perform the techniques pursuant to program instructions in firmware, memory, other storage, or a combination. Such special-purpose computing devices may also combine custom hard-wired logic, ASICs, or FPGAs with custom programming to accomplish the techniques. The special-purpose computing devices may be desktop computer systems, portable computer systems, handheld devices, networking devices or any other device that incorporates hard-wired and/or program logic to implement the techniques.

For example, FIG. 4 is a block diagram that illustrates a computer system 400 upon which an embodiment of the invention may be implemented. Computer system 400 includes a bus 402 or other communication mechanism for communicating information, and a hardware processor 404 coupled with bus 402 for processing information. Hardware processor 404 may be, for example, a general purpose microprocessor.

Computer system 400 also includes a main memory 406, such as a random access memory (RAM) or other dynamic storage device, coupled to bus 402 for storing information and instructions to be executed by processor 404. Main memory 406 also may be used for storing temporary variables or other intermediate information during execution of instructions to be executed by processor 404. Such instructions, when stored in non-transitory storage media accessible to processor 404, render computer system 400 into a special-purpose machine that is customized to perform the operations specified in the instructions.

Computer system 400 further includes a read only memory (ROM) 408 or other static storage device coupled to bus 402 for storing static information and instructions for processor 404. A storage device 410, such as a magnetic disk, optical disk, or solid-state drive is provided and coupled to bus 402 for storing information and instructions.

Computer system 400 may be coupled via bus 402 to a display 412, such as a cathode ray tube (CRT), for displaying information to a computer user. An input device 414, including alphanumeric and other keys, is coupled to bus 402 for communicating information and command selections to processor 404. Another type of user input device is cursor control 416, such as a mouse, a trackball, or cursor direction keys for communicating direction information and command selections to processor 404 and for controlling cursor movement on display 412. This input device typically has two degrees of freedom in two axes, a first axis (e.g., x) and a second axis (e.g., y), that allows the device to specify positions in a plane.

Computer system 400 may implement the techniques described herein using customized hard-wired logic, one or more ASICs or FPGAs, firmware and/or program logic which in combination with the computer system causes or programs computer system 400 to be a special-purpose machine. According to one embodiment, the techniques herein are performed by computer system 400 in response to processor 404 executing one or more sequences of one or more instructions contained in main memory 406. Such instructions may be read into main memory 406 from another storage medium, such as storage device 410. Execution of the sequences of instructions contained in main memory 406 causes processor 404 to perform the process steps described herein. In alternative embodiments, hard-wired circuitry may be used in place of or in combination with software instructions.

The term "storage media" as used herein refers to any non-transitory media that store data and/or instructions that cause a machine to operate in a specific fashion. Such storage media may comprise non-volatile media and/or volatile media. Non-volatile media includes, for example, optical disks, magnetic disks, or solid-state drives, such as storage device 410. Volatile media includes dynamic memory, such as main memory 406. Common forms of storage media include, for example, a floppy disk, a flexible disk, hard disk, solid-state drive, magnetic tape, or any other magnetic data storage medium, a CD-ROM, any other optical data storage medium, any physical medium with patterns of holes, a RAM, a PROM, and EPROM, a FLASH-EPROM, NVRAM, any other memory chip or cartridge.

Storage media is distinct from but may be used in conjunction with transmission media. Transmission media participates in transferring information between storage media. For example, transmission media includes coaxial cables, copper wire and fiber optics, including the wires that comprise bus 402. Transmission media can also take the form of acoustic or light waves, such as those generated during radio-wave and infra-red data communications.

Various forms of media may be involved in carrying one or more sequences of one or more instructions to processor 404 for execution. For example, the instructions may initially be carried on a magnetic disk or solid-state drive of a remote computer. The remote computer can load the instructions into its dynamic memory and send the instructions over a telephone line using a modem. A modem local to computer system 400 can receive the data on the telephone line and use an infra-red transmitter to convert the data to an infra-red signal. An infra-red detector can receive the data carried in the infra-red signal and appropriate circuitry can place the data on bus 402. Bus 402 carries the data to main memory 406, from which processor 404 retrieves and executes the instructions. The instructions received by main memory 406 may optionally be stored on storage device 410 either before or after execution by processor 404.

Computer system 400 also includes a communication interface 418 coupled to bus 402. Communication interface 418 provides a two-way data communication coupling to a network link 420 that is connected to a local network 422. For example, communication interface 418 may be an integrated services digital network (ISDN) card, cable modem, satellite modem, or a modem to provide a data communication connection to a corresponding type of telephone line. As another example, communication interface 418 may be a local area network (LAN) card to provide a data communication connection to a compatible LAN. Wireless links may also be implemented. In any such implementation, communication interface 418 sends and receives electrical, electromagnetic or optical signals that carry digital data streams representing various types of information.

Network link 420 typically provides data communication through one or more networks to other data devices. For example, network link 420 may provide a connection through local network 422 to a host computer 424 or to data equipment operated by an Internet Service Provider (ISP) 426. ISP 426 in turn provides data communication services through the world wide packet data communication network now commonly referred to as the "Internet" 428. Local network 422 and Internet 428 both use electrical, electromagnetic or optical signals that carry digital data streams. The signals through the various networks and the signals on network link 420 and through communication interface 418, which carry the digital data to and from computer system 400, are example forms of transmission media.

Computer system 400 can send messages and receive data, including program code, through the network(s), network link 420 and communication interface 418. In the Internet example, a server 430 might transmit a requested code for an application program through Internet 428, ISP 426, local network 422 and communication interface 418.

The received code may be executed by processor 404 as it is received, and/or stored in storage device 410, or other non-volatile storage for later execution.

3. Fertility Advisor

3.1. Received Data

Figure 5:
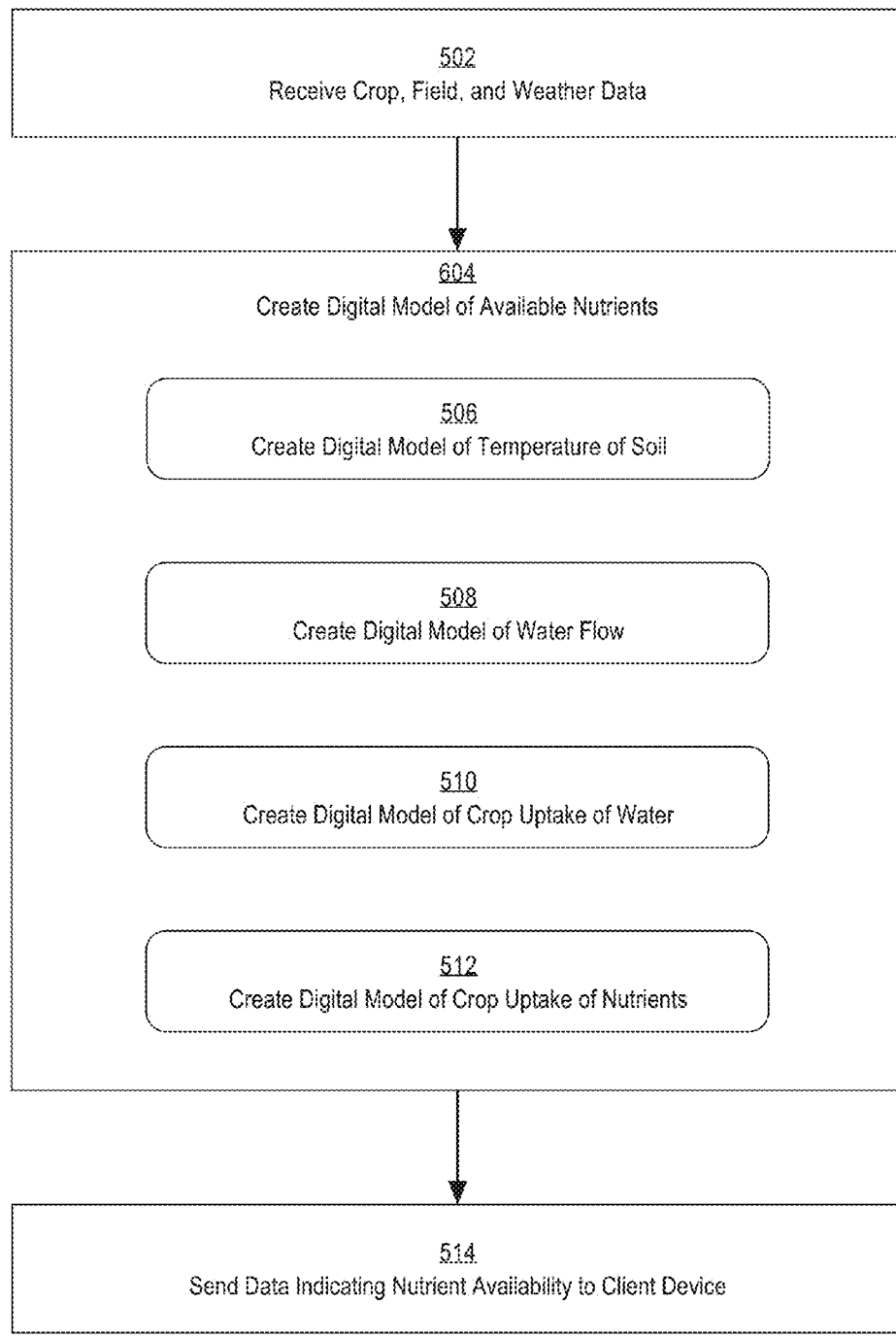
FIG. 5 depicts an example method of creating a digital model of nutrient availability in soil.

FIG. 5 depicts an example method of creating a digital model of nutrient availability in soil.

At step 502, crop, field, and weather data is received. For example, agricultural intelligence computer system 130 may receive field data 106 from field manager computing device 104 and/or external data 110 from external data server computer 108. Field data 106 may include information relating to the field itself, such as field names and identifiers, soil types or classifications, tilling status, irrigation status, soil composition, nutrient application data, farming practices, and irrigation data. As used herein, a 'field' refers to a geographically bounded area comprising a top field which may also comprise one or more subfields. Field data 106 may also include information relating to one or more current crops, such as planting data, seed type or types, relative maturity levels of planted seed or seeds, and seed population. Additionally, field data 106 may include information relating to historical harvest data including crop type or classification, harvest date, actual production history, yield, grain moisture, and tillage practices.

In an embodiment, field data 106 is received from field manager computing device 104. For example, agricultural intelligence computer system 130 may cause display of an interface on field manager computing device 104 for inputting information, such as the bounds of the field, the types of seed planted, and other crop and field related information. Additionally and/or alternatively, soil and seed samples may be received and analyzed at the field and field manager computing device 104 may send the analyzed data to agricultural intelligence computer system 130. For example, an implement on the one or more fields may be used to extract soil from the field and determine the percentage of sand, silt, clay, and organic carbon in the soil. The soil data may then be sent from the implement to field manager computing device 104 or directly to agricultural intelligence computer system 130.

External data 110 may include any additional data about the field, the one or more crops, weather, precipitation, meteorology, and/or soil and crop phenology. Weather, precipitation, and meteorology may be received as current temperature/precipitation data and future forecast data for the one or more fields. Additionally and/or alternatively, the current temperature/precipitation data and forecast data may include data at specific observation posts that is interpolated to locations in between the observation posts, such as in Non-Provisional application Ser. No. 14/640,900 the entire contents of which are incorporated by reference as if fully set forth herein. External data 110 may also include soil data for the one or more fields. For example, the Soil Survey Geographic database (SSURGO) contains per layer soil data at the sub field level for areas in the United States, including percentage of sand, silt, and clay for each layer of soil. In an embodiment, external data 110 includes data received from SSURGO or other sources of soil data. In an embodiment, external data is supplemented with grower data and/or laboratory data. For example, soil taken from the one or more fields may be used to adjust the external data received from SSURGO where the external data is inaccurate. Additionally, where some information is likely inaccurate, such as where certain statistics of a soil are inconsistent with other statistics of the soil, surrounding data and/or soil data from the one or more fields may be used to estimate the correct statistics.

3.2. Nutrient Availability Model

At step 502, a digital model of available nutrients in the soil of the one or more fields is created. For example, fertility advisor module 136 may create a digital model of available nutrients in the soil based on one or more other digital models relating to a crop on the one or more fields, the soil temperature of the one or more fields, and/or the flow of water through the one or more fields. Nutrient availability refers to nutrients in the soil that are available to be used by the one or more crops on the one or more fields. Nutrients may exist within the soil surrounding a crop, but not be available to the crop for a variety of reasons. For example, some of the nutrients within the soil may be too deep in the soil for the crop to reach. Some of the nutrients may be lost before the crop can use it. For example, nitrogen in the soil may be lost to leaching, denitrification, or volatilization. Additionally, some nutrients may be unavailable to the crop based on the ability of the soil to transfer the nutrients to the crop based on soil temperature or soil moisture. The digital model of available nutrients takes into account not just the nutrients in the system, but the nutrients that can be accessed and utilized by the crop due to a variety of factors.

Figure 6:
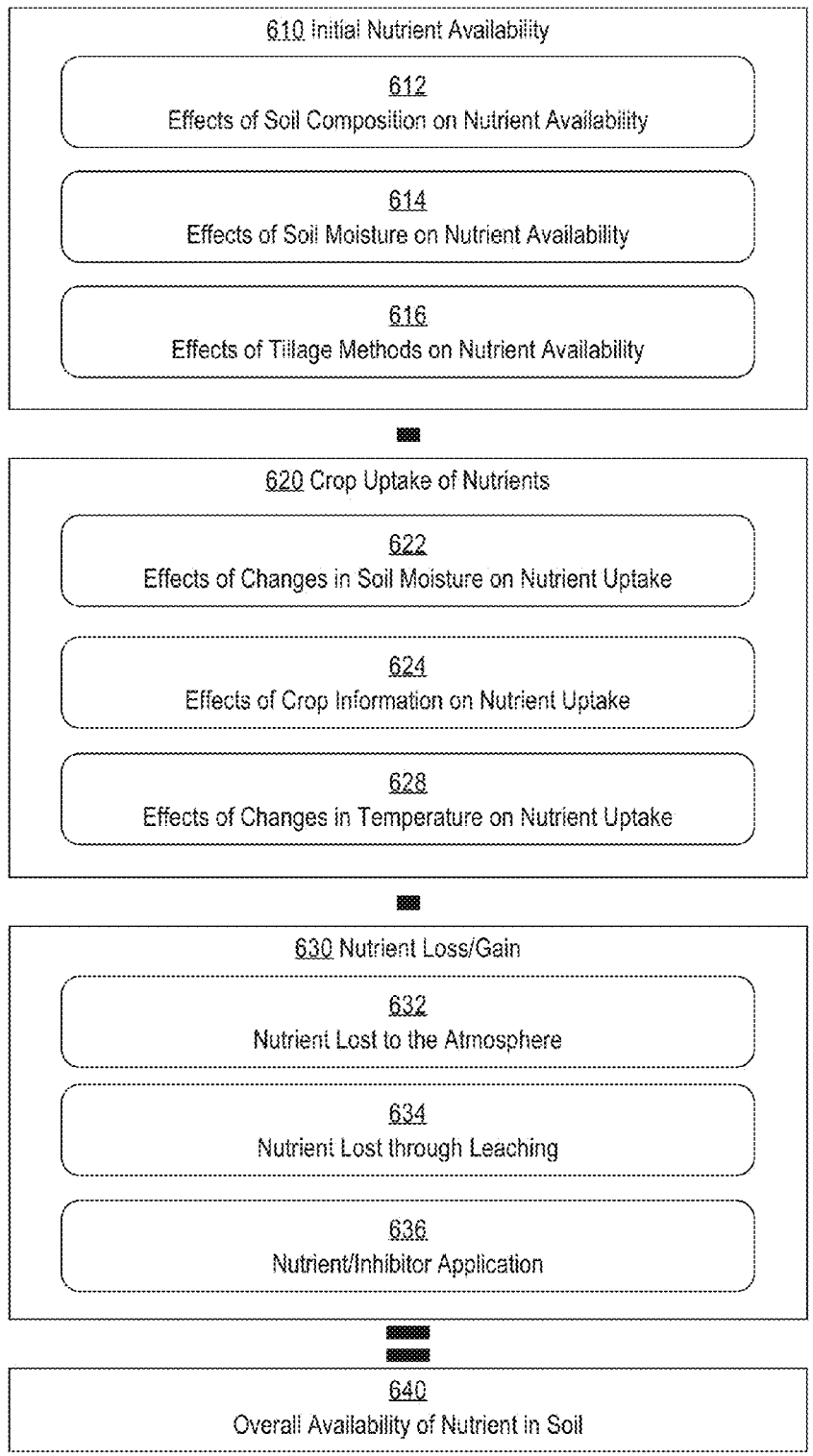
FIG. 6 depicts an example method of combining data from a plurality of digital models to determine nutrient availability in soil.

FIG. 6 depicts an example method of combining data from a plurality of digital models to determine nutrient availability in soil. The method depicted in FIG. 6 takes into account initial nutrient availability 610, crop uptake of nutrients 620, and nutrient loss/gain 630 to determine overall availability of nutrient in soil 640. Each of initial nutrient availability 610, crop uptake of nutrient 620, and nutrient loss/gain 630 may be determined by fertility advisor module 136 based on one or more digital models relating to the one or more crops and the one or more fields. For example, one or more other modules may use as input field data 106 and external data 110 to create interdependent models of temperature, water flow, and crop interactions with soil. Modeling techniques used by the one or more modules are described in more detail herein.

3.2.1. Initial Nutrient Availability

Initial nutrient availability 610 may be determined based on effects of soil composition on nutrient availability 612, effects of soil moisture on nutrient availability 614, and effects of tillage methods on nutrient availability 616. Soil composition, soil moisture, and tillage methods may also have continuing effects on the model of nutrient availability. Thus, in an embodiment, the soil moisture, soil composition, and tillage methods are factored into each measurement of nutrient availability along with the initial estimate of nutrients available in the system.

The soil composition may be identified as a combination of soil layer data received from external data server computer 108 and manure data received from field manager computing device 104. Manure data may describe a composition of manure with respect to each nutrient. For example, manure can be generally broken up into three components: inorganic nitrogen, labile organic nitrogen, and stable organic nitrogen. Labile organic nitrogen decomposes within roughly one year while stable organic nitrogen tends to decompose over the course of five to ten years. Thus, the specific composition of the manure not only affects the current nitrogen available to a plant, but the availability of nitrogen in the soil over time. In an embodiment, agricultural intelligence computer system 130 receives an indication of a type of manure used on the one or more fields from field manager computing device 104. Agricultural intelligence computer system 130 may determine the composition of the manure based on the input manure type. For example, agricultural intelligence computer system 130 may access a database that lists types of manure with the composition of the type of manure. In other embodiments, a device may be used to analyze the nutrient composition in a sample of the manure used on the field. The analysis of the nutrient composition in the sample may then be sent to agricultural intelligence computer system 130.

Effects of soil moisture on nutrient availability 614 may be used to determine an initial availability of nutrients to the one or more crops and to adjust the availability of nutrients to the one or more crops over time. Soil moisture may be determined by hydrology module 144 as described in more detail below. The soil moisture initially affects the lateral transport of nutrients to the crop. For example, when the soil is sufficiently moist, lateral transport of nitrogen to the roots of the crop is more effective. Thus, if all other conditions are equivalent, fertility advisor module 136 may determine that more nitrogen is initially available in a field with high moisture content than a field with low moisture content. Additionally, as the soil moisture content decreases, fertility advisor module 136 may determine that the nitrogen available to the crop decreases. When the soil moisture content increases, fertility advisor module 136 may determine that the nitrogen available to the crop increases.

Effects of tillage methods on nutrient availability 616 may be determined by fertility advisor module 136 based on field data 106 received from field manager computing device 104. Tillage refers to the agricultural preparation of a field. Different tillage methods have different effects on the nutrients available in different layers of the soil. For example, intense tillage methods, such as moldboard plow tillage leave behind extremely little residue from the prior harvesting. The residue pools from the prior harvesting may contain varying levels of nutrients based, at least in part, on the prior planted crop and the remaining nutrients available in the top soil at harvest. Thus, the method of tillage prior to the planting of a new crop may impact the nutrient availability in the remaining soil. In an embodiment, agricultural intelligence computer system 130 receives an indication of the type of tillage method used on the soil from field manager computing device 104. For example, presentation layer 134 may cause display of an interface for inputting a tillage type on field manager computing device 104. In an embodiment, the display accepts input identifying a tillage type from a list of tillage types, such as through a drop down list which includes various tillage types, a date of harvest for a prior copy, and one or more dates of tillage. In additional embodiments, the display accepts input which specifies a tillage depth, tillage implements, and other variables specific to an instance of tillage using a particular method.

3.2.2. Nutrient Losses and Gains

Nutrients available in the soil are reduced by crop uptake of nutrients 620. The amount of nutrients accessed and used by a crop may vary based on effects of changes in soil moisture on nutrient uptake 622, effects of crop information on nutrient uptake 624, and effects of changes in soil temperature on nutrient uptake 626. In an embodiment, crop module 146 models the uptake of nutrients based, at least in part, on temperature, moisture content, and crop information such as crop type. Temperature and moisture content of the soil may be modeled by temperature module 142 and hydrology module 144 respectively. As nutrient uptake by the crop is partially dependent on the nutrients available to the crop, fertility advisor module 136 may update crop uptake of the nutrients 620 iteratively as the availability of nutrients decreases. The crop model is described in more detail herein.

Additionally, fertility advisor module 136 may estimate nutrient loss/gain 630 from elements outside of the crop. Nutrient loss/gain 630 includes nutrient lost to the atmosphere 632, nutrient lost through leaching 634, and nutrient and enhanced efficiency agrochemical application 636. Nutrients may be lost to the atmosphere through a number of chemical processes. For example, nitrogen may be lost to the atmosphere through a process called denitrification where $NO_3$ is converted into $N_2$ and is lost to the atmosphere. In an embodiment, fertility advisor module 136 models the loss of nitrogen through denitrification based on field data 106 received from field manager computing device 104 and/or external data 110 received from external data server computer 108. The amount of nitrogen lost through denitrification may be modeled as a factor of the temperature of the soil and the moisture content of the soil. Additionally, nitrogen may be lost to the atmosphere through volatilization, a process that involves the conversion of ammonium ($NH_4$) to ammonia gas ($NH_3$). Fertility advisor module 136 may model the loss of nitrogen through volatilization as a function of soil moisture, temperature, and pH of the soil. Thus, fertility advisor module 136 may use the models of temperature and water flow to determine a temperature and moisture content at each instance and use the models of temperature and water flow to determine how much of each nutrient is lost through chemical processes such as through denitrification and volatilization. In doing so, fertility advisor module 136 may track amounts of each form of each nutrient, such as amounts of nitrogen available as $NO_3$ and amounts of nitrogen available as $NH_4$. By tracking the different types of nutrients available in the model, fertility advisor module 136 may accurate model the amount of each nutrient lost by each process.

Nutrients may be lost through leaching when the nitrogen is transferred downward through the soil and lost to the system. The amount of a nutrient lost through leaching may be determined as a function of the moisture content of the soil. As higher moisture content increases the flow of some nutrients through the soil, thereby increasing the amount of the nutrients available to a crop, the increased flow also increases the amount of the nutrients that flows downward, thereby decreasing the amount of nutrients available to the system. Thus, as the moisture content increases, a higher percentage of the nutrients in the soil may be identified as being available while the total amount of the nutrients in the soil decreases. As fertility advisor module 136 models the nutrient availability over time, fertility advisor module 136 may take into account the increased percentage of each nutrient available while subtracting a total amount of each nutrient lost through leaching.

Fertility advisor module 136 may be further programmed or configured to account for nutrients added to the system or nutrients that are protected through the application of enhanced efficiency agrochemicals. Nutrients may be added to the system through application of fertilizer or ammonia to the fields. Fertility advisor module 136 may model the movement of nutrients through the one or more fields. For example, fertility advisor module 136 may model the absorption and desorption of $NH_4+$ to and from solid mineral surfaces, the conversion from aqueous ammonium to aqueous ammonia, and the exsolution of dissolved ammonia to produce ammonia gas. Each time fertility advisor module 136 receives an indication that a nutrient has been added to the system, fertility advisor module 136 may add the nutrient to the existing model of nutrients in the system. For example, fertility advisor module 136 may add the new nitrogen values to the current nitrogen values for the top layer of the soil and update the model of nitrogen availability at maturity of the one or more crops based on the interactions of the newly added nitrogen with the current system.

Enhanced efficiency agrochemicals are chemicals that may be applied to the one or more fields to either improve the efficiency of one of the chemicals within the field or protect one or more of the chemicals from loss. For example, nitrogen stabilizers, such as nitrapyrin, may be added to the system through direct application or through application as part of an ammonium based fertilizer. Nitrapyrin can reduce the nitrification rate in soils, which in some cases can reduce subsequent leaching. In an embodiment, fertility advisor module 136 tracks the concentration of enhanced efficiency agrochemicals, such as nitrapyrin, over time. For example, a state variable may be set to 1 at the application of nitrapyrin to indicate a fresh application of nitrapyrin. As long as the concentration stays above a specific threshold, such as 0.9, all nitrification may be assumed to be blocked. Fertility advisor module 136 may track the nitrapyrin decay over time and introduce leaching due to nitrification when the concentration is reduced past the specific threshold. When the state value equals zero, fertility advisor module 136 may determine that no nitrification is blocked from the initial application of nitrapyrin. While the present disclosure describes tracking of nitrapyrin, similar methods may be used to track the concentration and effect of other enhanced efficiency agrochemicals.

In an embodiment, fertility advisor module 136 updates the nutrient availability in the one or more fields in response to receiving an indication that one or more nutrients and/or enhanced efficiency agrochemicals have been added to the field. Presentation layer 134 may cause display of an interface on field manager computing device 104 for entering data indicating an application of one or more nutrients and/or enhanced efficiency agrochemicals to the one or more fields. In response to receiving an indication that a nutrient has been added to the one or more fields, fertility advisor module 136 may update the nutrient availability to the crops and model the flow of the added nutrient through the one or more fields. In response to receiving an indication that enhanced efficiency agrochemicals, such as nitrapyrin inhibitors, have been added to the field, fertility advisor module 136 may update the models of nutrient loss to account for the enhanced efficiency agrochemicals, such as reducing nitrogen loss due to nitrogen protected by the nitrapyrin inhibitors.

Fertility advisor module 136 may determine overall availability of nutrient in soil 640 as a combination of the initial nutrients and added nutrients minus the lost nutrients and the nutrients used by the one or more crops. Fertility advisor module 136 may estimate overall availability of nutrients in soil 640 for a lifetime associated with one or more crops on the one or more fields. Based on models of the flow of water, changes in temperature, and uptake of nutrients by the crop, fertility advisor module 136 determines the nutrients available to a crop at each stage of the crop's development. Fertility advisor module 136 may also be programmed or configured to determine whether, based on current data, the one or more fields will have a surplus or shortfall of each nutrient when the one or more crops reach maturity. Additionally, fertility advisor module 136 may simulate applications of nutrients and/or water at different stages of development to determine optimal times to add water or nutrients to the system in order to increase the amount of nutrients available to a crop when the crop reaches maturity.

3.3. Temperature Model

Referring to FIG. 5, at step 506 a digital model of temperature of soil in the one or more fields is created. For example, temperature module 142 may model changes in the soil temperature for the one or more fields over the course of the development of the crop. The models of temperature may be broken up by soil layer or modeled as a continuous distribution of temperature through the soil. The temperatures for each soil layer at each period of time may be used by fertility advisor module 136 to determine the flow of nutrients through the soil. For example, volatilization of nitrogen increases as temperature increases. Thus, as the temperature of the soil rises, fertility advisor module 136 may estimate a larger loss of nitrogen through volatilization. The temperatures for each soil layer may also be used by hydrology module 144 to determine the flow of water through the soil and by crop module 146 to determine the uptake of nutrients by the one or more crops, as described in more detail herein.

Soil temperature is largely dependent on solar radiation, soil composition, and moisture content of the soil. Thus, temperature module 142 may take as input field data 106, external data 110, and outputs from fertility advisor module 136 and hydrology module 144. External data 110 may include current measurements of temperature as well as forecasts of future temperatures. If temperature data is unavailable in the location of the one or more fields or at a granularity that may be used by the one or more fields, temperature module 142 may interpolate the current temperatures or temperature forecasts, such as in Non-Provisional application Ser. No. 14/640,900. For periods of time where temperature forecasts are unavailable, temperature module 142 may use class averages for temperature for those periods of time. For example, if maximum temperatures for winter months in the location of the one or more fields tend to range from 65° F. to 75° F., temperature module 142 may utilize the range to estimate the maximum temperature for each day over the winter months. Temperature module 142 may estimate temperatures for future months at a higher level of granularity, based in part on current weather patterns. Thus, if temperatures in a specific region appear to be increasing uniformly, an increase in current maximum temperatures may cause temperature module 142 to estimate an increase in maximum temperatures for future months. Temperature module 142 may continuously alter estimates of temperature as more data becomes available. For example, estimates for the temperature in January that are made in July may be updated over time such that in December, the estimates for the temperatures in January are based on current temperature forecasts in addition to the estimates made in July.

In an embodiment, temperature module 142 is programmed or configured to estimate incoming solar radiation on the one or more fields based on forecasts of minimum and maximum temperature. For example, temperature module 142 may take as input the minimum and maximum temperatures in a specific location for consecutive days and determine the amount of incoming solar radiation based on the differences between the upcoming temperatures and the prior temperatures. For example, if on a first night the temperature drops to 50° F. and the temperature for the next day is 65° F., temperature module 142 may estimate the amount of solar radiation required to heat the specific location by 15° F. and to maintain the current temperature throughout the day. The resultant estimated solar radiation may be modeled as incident on the soil for the one or more crops. In an embodiment, temperature module 142 is further programmed or configured to take into account freezes and snowpack in updating temperature estimates. For example, snowpack creates an insulating effect, thereby reducing the changes of temperature based on incident solar radiation. Temperature module 142 may reduce the changes in temperature of the soil based on solar radiation in response to identifying snowpack on the one or more fields.

In an embodiment, external data 110 includes estimates of soil temperature by layer. Agricultural intelligence computer system 130 may receive models of temperature for soil layers from a database of soil temperatures estimated over a large region. Temperature module 142 may then alter the received temperature estimates based on soil composition, moisture content, and snowpack information for the one or more fields. For example, a received model may generally estimate temperature for a large spatial area based on common data, but would not be able to take into account the current moisture content of the soil or the chemical composition of the soil without receiving input specifying tillage methods, irrigation application, nutrient application, enhanced efficiency agrochemical application, or other field specific information. Thus, temperature module 142 may be programmed or configured to take as input general temperature estimates for one or more fields and update the temperature estimates based, at least in part, on estimated moisture content and field data 106 received from field manager computing device 104. Additionally, temperature module 142 may be programmed or configured to recognize snow conditions, such as likely snowpack, and update the received estimates for soil temperate based on the reduction of temperature change created by the snowpack. For example, temperature module 142 may receive a forecast that indicates a certain amount of snow for a given location and estimate snow build up based on the forecast.

In an embodiment, temperature module 142 updates temperature estimates based on information received from other models which use temperature as an input. For example, soil temperature may be partially affected by moisture content within the one or more fields. Temperature module 142 may thus use the output from hydrology module 144 to determine the changes to the temperature of the soil. In some cases, the inverse is also true. For example, the flow rate of water into the soil may be partially dependant on the temperature of the soil. Thus, at a given time, multiple models may work concurrently. For example, at a given time, temperature module 142 may determine a current temperature based on the current moisture content of the soil and hydrology module 144 may determine a current flow rate of water into the soil based on the current soil temperature. At a second given time, hydrology module 144 may estimate the current moisture content of the soil based on the determined flow rate and send the current moisture content to temperature module 142 which then determines the temperature at the second given time based on the moisture content at the second given time.

3.4. Hydrology Model

Referring to FIG. 5, at step 508, a digital model of water flow is created. For example, hydrology module 144 may use digitally programmed logic to create a model of the flow of water through the one or more fields based, at least in part, on weather data received from external data server computer 108, temperature data produced by temperature module 142, and soil data received from field manager computing device 104 and external data server computer 108. Weather data may include forecasts for precipitation over a specific period of time. For example, a weather forecast may include precipitation values with a fourteen day lead time. In an embodiment, agricultural intelligence computer system 130 creates improved precipitation forecasts from the received data, such as in Non-Provisional application Ser. No. 14/681,886 the entire contents of which are incorporated by reference as if fully set forth herein.

In an embodiment, agricultural intelligence computer system 130 executes digitally programmed logic to create precipitation forecasts for periods of time where data is unavailable. For example, agricultural intelligence computer system 130 may use average precipitation values from the past few years to estimate the likely precipitation for the one or more crops over the development of the one or more crops. In an embodiment, the estimates of precipitation are constrained by current available precipitation data. For example, agricultural intelligence computer system 130 may identify a correlation between an absence of rain in June and heavy storms in July in a specific location. Thus, if the weather data for June indicates no precipitation, agricultural intelligence computer system 130 may determine that a storm is likely to occur in July. Additionally, agricultural intelligence computer system 130 may identify a likelihood of precipitation and likely intensity of precipitation for areas with no data. For example, if precipitation data is only available at observation locations or at high levels of granularity, agricultural intelligence computer system 130 may interpolate the data to each specific location, such as in Non-Provisional application Ser. No. 14/798,256, the entire contents of which are incorporated by reference as if fully set forth herein.

The movement of water may be broken down into two stages. The first stage of water movement corresponds to surface water processes. The goal of the first stage is to estimate surface storages and fluxes. For example, water may impact the one or more fields due to weather conditions, such as precipitation, or through physical intervention, such as scheduled watering of the one or more fields. During this first stage, hydrology module 144 may model the immediate effects of the water on the field. Immediate effects may include snowpack, storage in plant residue, storage in crop biomass, infiltration, ponding, run off, evaporation from biomass, evaporation from residue, and snow ablation, such as sublimation, melting, and wind transport.

In an embodiment, agricultural intelligence computer system 130 uses digitally programmed logic to model the first stage of water movement. First, agricultural intelligence computer system 130 partitions the precipitation in solid precipitation, or snow, and liquid precipitation, or water. For example, based on a measurement of the current temperature at the one or more fields, agricultural intelligence computer system 130 may determine a percentage of the precipitation that is solid and a percentage of the precipitation that is liquid. Any solid precipitation is added to a model of a snowpack layer. Agricultural intelligence computer system 130 may simulate freezing and thawing processes for the snowpack as a function of weather and soil conditions. Next, agricultural intelligence computer system 130 simulates interception of rainfall by various aboveground biomass components as a function of biomass types, amount of biomass, and weather conditions. Agricultural intelligence computer system 130 may also model the lateral redistribution of liquid water that reaches the soil surface as a function of weather conditions, aboveground biomass types, an amount of aboveground biomass, soil properties, and soil moisture. Evaporation of water from the soil may be simulated as a function of weather conditions, aboveground biomass types, an amount of aboveground biomass, soil properties, and soil moisture. Ponding may be simulated for any precipitation that exceeds other redistribution rates.

In a second stage, water that is absorbed into the field moves around below the earth. During this second stage, hydrology module 144 may model the movement of water in the field. In an embodiment, the second stage of water flow begins when hydrology module 144 determines that water has flowed past an upper boundary separating the surface layer of the soil from the subsurface layer of the soil. Hydrology module 144 may specify an upper boundary condition for the subsurface soil layer according to weather conditions, simulated soil conditions, and simulated biomass condition. Hydrology module 144 may use a variable flux boundary condition to represent rates of water flow across the boundary. Additionally and/or alternatively, hydrology module 144 may use a variable head boundary condition to represent water flow across the boundary, such as when hydrology module 144 detects ponding of water. For example, hydrology module 144 may be programmed or configured to dynamically switch between the variable flux boundary condition and the variable head boundary condition in a particular region of the one or more fields in response to identifying ponding of water in the particular region.

Hydrology module 144 may also specify a lower boundary condition for the subsurface soil layer separating the subsurface soil layer from a drainage layer. For example, if agricultural intelligence computer system 130 receives data indicating that the one or more fields are tile drained, hydrology module 144 may specify a constant head lower boundary condition to represent the effect of drainage into tile lines. If agricultural intelligence computer system 130 determines that the one or more fields are not drained, hydrology module 144 may specify a variable flux lower boundary condition to represent free drainage from the subsurface soil layer to a deeper water table. In an embodiment, hydrology module 144 simulates multiple water tables below the subsurface layer, such as a shallower water table and a deeper water table. Hydrology module 144 may identify the deeper water tables based on field data 106, such as through remote sensors or soil moisture probes, or based on external data 110, such as through estimates of the likelihood of the presence of a shallow water table using soil data received from a soil database.

During the second stage, hydrology module 144 may model losses of water through movement beyond the lower boundary and through evapotranspiration. Evapotranspiration is an estimate of water loss through a combination of transpiration transpiration. Evaporation and transpiration losses may be assigned to each soil layer for each time step of a plurality of time steps. For example, hydrology module 144 may estimate water absorption, transpiration, and evaporation for a particular crop at each subsurface layer multiple times at static time intervals or at dynamically changing time intervals. In an embodiment, remote sensor data may be utilized to improve evapotranspiration estimates. For example, a soil moisture probe may be utilized to identify, at a particular region of the one or more fields, the actual soil moisture at each subsurface soil layer. Hydrology module 144 may use the soil moisture probe data to correct evapotranspiration estimates for the subsurface soil layers in other portions of the one or more fields.

To model the flow of water beneath the soil surface, hydrology module 144 may apply Darcy's Law which states that the flow rate of water into a saturated permeable matrix is equal to the product of the hydraulic gradient and the sediment hydraulic conductivity. As an example, for unsaturated sediments, such as most soils, the Buckingham-Darcy equation describes the flow rate of water through the following equation:

$$q = K(\theta, T) \cdot \left(\frac{dh}{dz} + 1\right)$$

where q is the flow rate, measured in mm/day, K is the hydraulic conductivity of the soil, measured in mm/day, and $$\frac{dh}{dz}$$

is the hydraulic head gradient. The hydraulic conductivity of soil describes the ease at which water can move through a porous space. The hydraulic conductivity of the soil is largely dependent on the physical properties of the soil, the current moisture content of the soil ($\theta$), and the temperature of the soil (T). The hydraulic head gradient describes a difference in potential between two locations scaled to their vertical distance. Water tends to flow from a location of lower potential to a location of higher potential. In this example, water flow is driven by two potentials, gravitational and matric. In other examples, the equation may be modified to take into account other potentials, such as osmotic potential or hydrostatic potential. For example, the following equation represents a subset of potentials that make up a total potential at a given location:

$$\psi_t = \psi_z + \psi_m + \psi_o + \psi_s$$

where $\psi_t$ is the total potential, $\psi_z$ is the potential due to gravity, $\psi_m$ is the matric potential, $\psi_o$ is the osmotic potential, and $\psi_s$ is the hydrostatic potential. The potential due to gravity describes the gravitational force of the liquid. The matric potential describes a force of the liquid due to water absorption and capillary action within the sediment matrix. The osmotic potential describes a force of the liquid due to the difference in salinity of the two locations. Finally, the hydrostatic potential describes a force of a liquid onto a second liquid in a saturated location.

3.4.1. Adaptive Time Steps

A first method of modeling the flow of water through the earth is by using the Richards equation. The Richards equation simultaneously solves two equations, Darcy's law and conservation of mass. The one dimensional Richards Equation attempts to determine the change in the moisture content based on the change in the flow rate of the liquid as follows:

$$\frac{d\theta}{dt} = \frac{d}{dz}\left(K(\theta, T) \cdot \left(\frac{dh}{dz} + 1\right)\right)$$

In solving both Darcy's law and conservation of mass within one equation, the Richards equation provides an accurate method for modeling the flow of water into unsaturated sediment. Because the Richards equation is a non-linear differential equation, exact solutions of the Richards equation only exist for extremely specialized conditions. Solving the Richards equation involves an iterative scheme, making the solution computationally expensive. Many implementations of the Richards equation tend to be inefficient or fail in edge cases.

A second method of modeling the flow of water through the earth is a bucket approach. The bucket approach models water flow by assuming that each layer of sediment acts as a bucket. As one bucket fills, the water pours into the next bucket beneath it, and so on. In many bucket approaches, water leaving the lowest bucket is completely lost to the system. The bucket approach, while physically unrealistic and therefore less accurate, may be implemented instead of the Richards equation because it is computationally lighter and can be implemented with less reliable data.

In an embodiment, hydrology module 144 uses a third approach for modeling the flow of water through the earth which is both computationally inexpensive and physically realistic. Instead of using the Richards equation to simultaneously solve Darcy's law and conservation of mass, hydrology module 144 may separate the Richards equation into a solution of the Buckingham-Darcy equation and a separate solution to the conservation of mass. For example, hydrology module 144 may separate the measure of water flow into various time steps and create measurements for each time step. The length of time steps may vary from twenty time steps per forcing step of a day to thousands of time steps per forcing step of a day.

Figure 7:
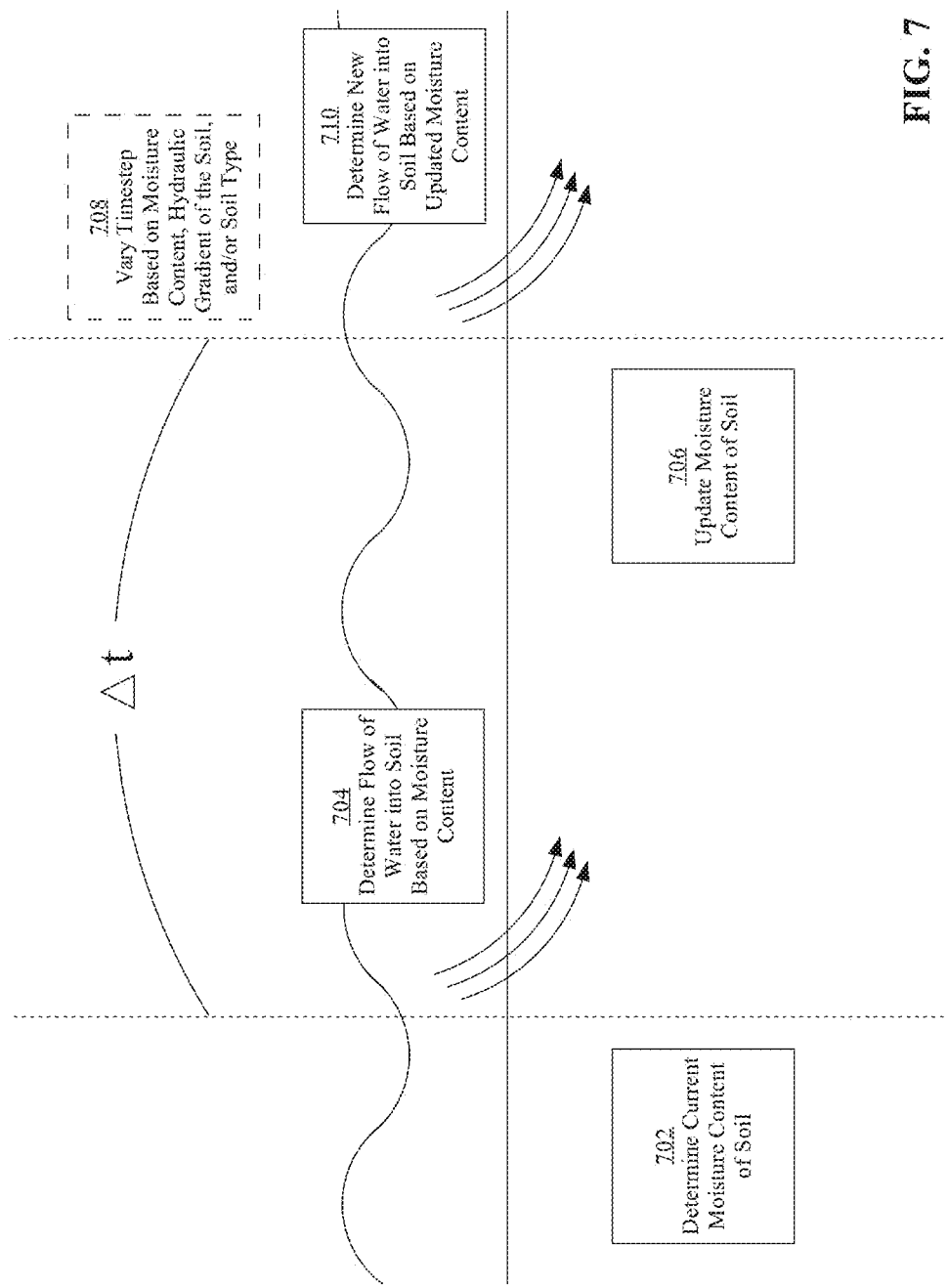
FIG. 7 depicts an example method for modeling the flow of water into soil.

FIG. 7 depicts an example method for modeling the flow of water into soil. At step 702, the current moisture content of the soil is determined. For example, hydrology module 144 may initially determine moisture content for soil based on the soil's properties and/or effects of prior weather conditions. In an embodiment, the moisture content of the soil is determined based on a previous moisture content of the soil, previous water availability, and prior flow of water into the soil.

At step 704, the flow of water into the soil is determined based on the current moisture content for a given time step, $\Delta t$. For example, hydrology module 144 may implement digitally stored logic to solve the Buckingham-Darcy equation. Hydrology module 144 may utilize parameterization techniques, discussed below, to determine the hydraulic conductivity and hydraulic head gradient in the Buckingham-Darcy equation based, at least in part, on known data about the soil and the current moisture content. The solution to the Buckingham-Darcy equation results in a determination of the rate of flow of water into the soil.

At step 706, the rate of flow of the water into the soil is used to update the moisture content of the soil. For example, hydrology module 144 may use digitally stored logic to determine the moisture content of the soil based on an assumption of a consistent flow of water based on the Buckingham-Darcy equation during the given time step of $\Delta t$. For instance, if hydrology module 144 determines that the rate of flow of the water into the soil is two millimeters an hour, then during a time step of one hour, hydrology module 144 may determine that two millimeters of water have entered the soil. The new moisture content of the soil is then determined based on the prior moisture content of the soil, the volume of soil receiving the water flow, and the total amount of water that has flowed into the soil.

In a simple embodiment, at step 710 a new flow of water into the soil is determined based on an updated moisture content for the next time step. In an embodiment, each time step is equivalent in length to the prior time step. For example, if a given day includes twenty four time steps, each time step would be set at an hour. Thus, at step 710, the processes of step 704 is repeated based on the updated moisture content. Hydrology module 144 may use the prior parameterization of the Buckingham-Darcy equation to determine the hydraulic conductivity and hydraulic head gradient based on the updated moisture content of the soil. For each time step, hydrology module 144 may repeat the process of determining the flow rate of water into the soil, determining the amount of water that has entered the soil, and updating the moisture content of the soil.

At step 708, in some embodiments, the time step is varied before the new determination of water flow into the soil. The variance of the time step creates stability in the process and ensures accurate results with minimal computational expense. A uniformly small time step would be computationally expensive because it would involve a large number of iterations of solving the Buckingham-Darcy equation and updating the moisture content of the soil. A uniformly large time step, while computationally inexpensive, becomes unstable during extreme weather conditions. For example, during a heavy storm, a large amount of water becomes available to the soil. In these situations, the moisture content of the soil may change extremely quickly, causing the flow of water into the soil to change rapidly. These large variances can lead to the instability in the calculations if small time steps are not used.

In an embodiment, hydrology module 144 varies the time step based on one or more factors, such as moisture content, hydraulic gradient of the soil, soil type, or extreme weather conditions. For example, if hydrology module 144 determines that the moisture content of the soil has risen or fallen by more than a threshold value during the prior time step, hydrology module 144 may vary the time step to account for the changing conditions. As another example, hydrology module 144 may store different time step lengths in association with different moisture contents and hydraulic conductivity. If the moisture content and hydraulic conductivity of the soil fall within parameters described by a first category, hydrology module 144 may implement a time step of a first length. If the moisture content and hydraulic conductivity fall into parameters described by a second category, hydrology module 144 may implement a time step of a second length. By increasing the length of the time steps during periods of less volatile conditions, agricultural intelligence computer system 130 is able to make more computationally efficient calculations of the flow of water into the soil.

In an embodiment, hydrology module 144 calculates the time step based on a variety of factors. For example, hydrology module 144 may factor in the current moisture content, the current hydraulic gradient between soil layers, and the current available water to determine whether the moisture content of the soil is likely to undergo dynamic changes. For example, hydrology module 144 may decrease the length of the time step in response to determining that the soil currently contains a high moisture content or that the hydraulic gradient between two layers of soil is relatively high, thereby indicating a large difference between the moisture content of a first layer of soil and a moisture content of a second layer of soil. Hydrology module 144 may also take into account different factors which have an effect on the flow of water into the soil when calculating the time step. For example, with all other conditions being equal, a uniform soil type may undergo less dynamic changes than a layered soil type. Hydrology module 144 may thus take into account the type of soil when estimating the new time step.

In an embodiment, the adaptive time step procedure favors larger time steps. For example, with a minimum time step length of twenty time steps per day, a median value time step length may be approximately thirty time steps per day with outliers in the thousands of time steps per day. The adaptive time step model may thus be implemented to accurately model moisture content during extreme and rare weather conditions while maintaining accurate estimates with a low computational cost during times of common weather conditions.

In one embodiment, hydrology module 144 determines whether to vary each time step. For example, hydrology module 144 may use digitally programmed logic to determine an optimal time step length based on the hydraulic conductivity and moisture content of the soil after each solution step. In other embodiments, hydrology module 144 determines whether to vary the time step at given intervals. For example, hydrology module 144 may use weather prediction data, current soil moisture, and current hydraulic conductivity of the soil to determine an optimal time step length for each time interval of a first day. Hydrology module 144 may then use weather prediction data, the last modeled soil moisture, and the last modeled hydraulic conductivity to determine the optimal time length for the next day.

In embodiments where the time interval is updated at specific intervals, such as once a day, automatic and manual overrides may exist to alter the time interval during unexpected or extreme weather conditions. Hydrology module 144 may be configured to determine that one or more factors have changed by more than a threshold value and, in response to determining that the one or more factors have unexpectedly changed by more than the threshold value, update the time interval. For example, hydrology module 144 may be configured to update the time interval at the end of each day. If during the middle of the day, hydrology module 144 determines that the soil moisture has increased by more than a threshold value, such as due to an unexpected storm or input from a client device indicating an application of water to the field, hydrology module 144 may cause the time interval to be updated based on the new information.

By applying the Buckingham-Darcy equation followed by an update to the soil moisture during adaptively changing time steps, hydrology module 144 creates a technical solution to the computational expense of prior techniques without suffering from the inaccuracies that occur due to the use of simpler techniques. The method described in FIG. 7 uses digitally implemented logic to significantly decrease the load on the CPU of agricultural intelligence computer system 130 by removing the iterative scheme required to solve a non-linear differential equation. By adaptively updating the time interval, hydrology module 144 preserves the computational efficiency of the technique without sacrificing accuracy during extreme conditions.

3.4.2. Parameterization

While the above described application of the Buckingham-Darcy equation is more accurate than less complex approaches, the parameterization of the Buckingham-Darcy equation may involve additional computations. For example, the Buckingham-Darcy equation uses as parameters the hydraulic conductivity of the soil and the sum of the pressures of the water to the soil. Because the implementation of the Buckingham-Darcy equation discussed above solves for the moisture content of the soil at each step, parameterization of the Buckingham-Darcy equation may be accomplished by creating a relationship between the unknown factors and the moisture content of the soil.

Differences in the moisture content of the soil can potentially have a large impact on the unsaturated hydraulic conductivity. The relationship between the moisture content of the soil at a given point and the hydraulic conductivity can be determined using one or more pedotransfer functions. The pedotransfer functions are statistical relationships between readily observable soil characteristics and hydraulic properties. For example, some pedotransfer functions accept as input a percentage of sand, silt, and clay of the soil to output parameters for a graph of hydraulic conductivity to moisture content. A pedotransfer function may be employed to determine the relationship between the soil moisture content and the hydraulic conductivity for one or more fields.

The total pressures on the soil may also vary with regards to the moisture content of the soil. As described above, the total potential for each soil layer can be described by the following equation:

$$\psi_t = \psi_z + \psi_m + \psi_o + \psi_s$$

The hydrostatic potential $\psi_s$ exists only in saturated conditions. In an embodiment, when the Buckingham-Darcy is being applied to non-saturated conditions, the hydrostatic potential $\psi_s$ may be ignored. In an embodiment, the salinity gradients may be assumed to be small depending on the location of the field. For example, hydrology module 144 may be configured to ignore the osmotic potential in areas that generally have low salt contents, but to factor in the salinity gradient for extreme conditions, such as in areas that employ drip irrigation, or in areas of high salt content. Thus, the total potential may be described as a combination of the gravitational potential $\psi_z$ and the matric potential $\psi_m$. The gravitational potential $\psi_z$, based on the forces applied by gravity, does not vary from field to field given an equivalent amount of water. Thus, the only unknown parameter for the total potential it is the matric potential $\psi_m$.

In an embodiment, hydrology module 144 may apply pedotransfer functions to determine the relationship between the soil moisture content and the matric potential. For example, some pedotransfer functions accept as input a percentage of sand, silt, and clay in the soil and output shape parameters for a function that describes the relationship between the matric potential and the soil moisture content. Additional inputs may include the bulk density of the soil and a percentage of organic carbon in the soil. In some embodiments, hydrology module 144 determines additional shape parameters for the matric potential curve to increase the accuracy of the estimate of the matric potential based on the moisture content of the soil.

Figure 8:
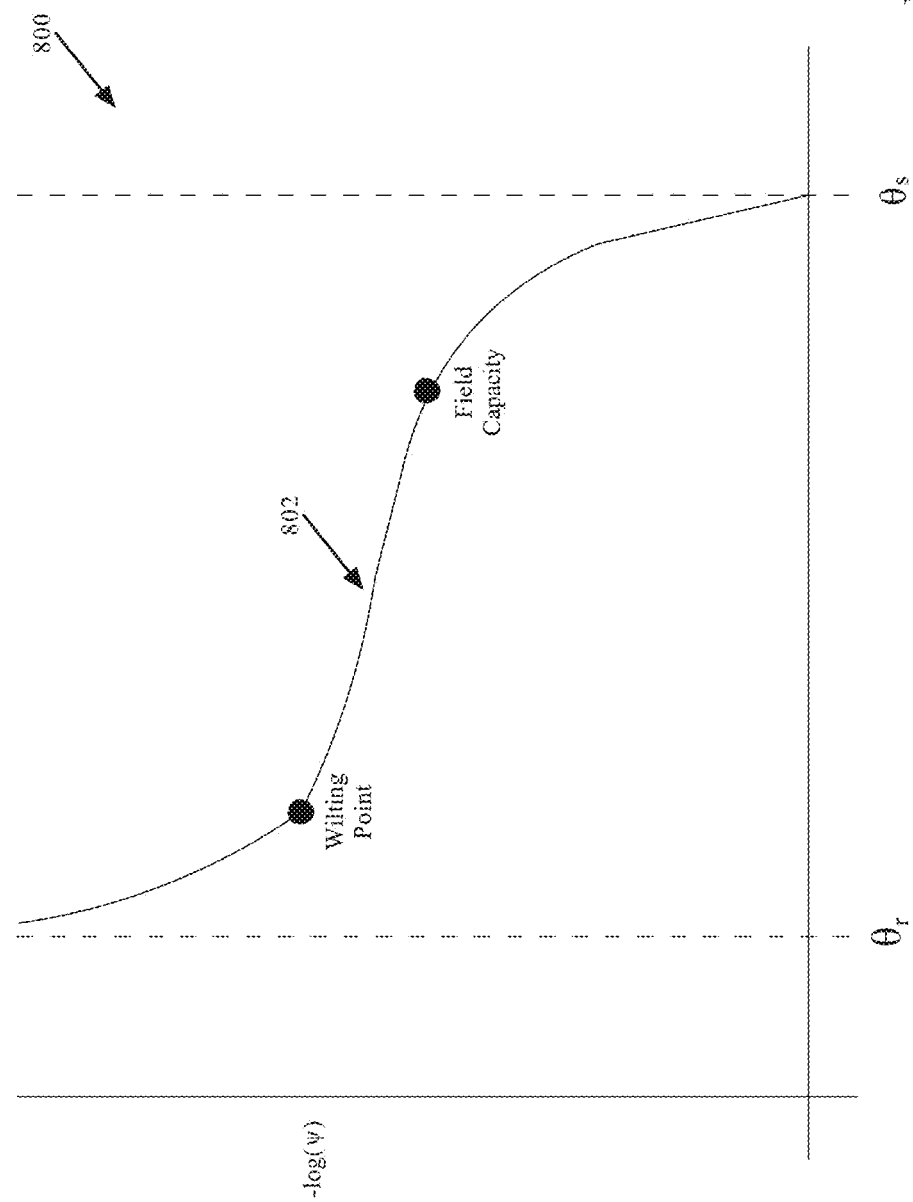
FIG. 8 depicts an example graph of the matric potential with respect to the moisture content of the soil.

FIG. 8 depicts an example graph of the matric potential with respect to the moisture content of the soil. Graph 800 includes matric potential curve 802. Matric potential curve 802 depicts a general relationship between the matric potential and the soil moisture content for various types of soil. Matric potential curve 802 is graphed as a relationship between the negative log of the matric potential and the moisture content. The shape of matric potential curve 802, for each soil type, may be defined by the Van Genuchten model as:

$$\theta(\psi) = \theta_r + \frac{\theta_s - \theta_r}{[1 + (\alpha|\psi|)^n]^{1-1/n}}$$

The horizontal bounds of the curve are determined by the residual moisture content $\theta_r$, and the saturated moisture content $\theta_s$. The residual moisture content defines a theoretical minimum amount of water that remains in the soil after drainage and evapotranspiration. The saturated moisture content defines a theoretical maximum amount of water that can be held in the soil. The saturated moisture content tends to be similar to the porosity of the soil. The remainder of the shape of the curve is defined by two parameters, $\alpha$ and n. For example, a higher $\alpha$, which is indicative of a coarse sediment, tends to create a sharper bend in the first curvature of matric potential curve 802. The location of the curvature is generally affected by changes to n. Additionally the matric potential curve 802 contains two points of constraint which are the wilting point and the field capacity.

In an embodiment, constraints on matric potential curve 802 are imposed based on prior measurements. For example, measurements of percentage sand, silt, clay, and organic carbon may be taken at the field or received from one or more outside sources. Additionally, the saturated moisture content for each type of soil may be measured for the specific field and stored in a database. As an example, SSURGO is a Soil Survey Geographic Database which contains the percentage of sand, silt, clay, and organic carbon for sub-surface layers of fields as well as the saturated moisture content, wilting point, and field capacity at each location. With percentage sand silt, clay, and organic carbon and the saturated moisture content, wilting point, and field capacity for each field known, established pedotransfer functions may be used to determine n and $\theta_r$.

In an embodiment, the received and calculated constraints are applied the matric potential curve 802. Once the constraints have been applied to matric potential curve 802, the only remaining constraint is the shape defined by $\alpha$. In an embodiment, hydrology module 144 generates multiple iterations of matric potential curve 802 under the imposed constraints with different values for alpha. Once the family of curves that conform to the imposed constraints is generated, hydrology module 144 may identify the alpha value which minimizes the sum of the square differences between the estimated wilting point and the estimated field capacity.

By applying measured and estimated constraints to matric potential curve 802 and using error minimization techniques to determine the last of the constraints, hydrology module 144 effectively creates a model that describes the matric potential and hydraulic conductivity for a field based on the moisture content of the field at a given time. To produce such a model traditionally, a laboratory would need undisturbed core samples from a field on which to iteratively apply known rates of flow and measure the response to the moisture content based on the known rate of flow.

In some embodiments, hydrology module 144 is configured to identify situations in which the model contains unlikely data. For example, in extremely rare situations, hydrology module 144 may create a model which includes two layers of extremely moist soil separated by a layer of extremely dry soil. Hydrology module 144 may be configured to recognize unlikely scenarios, such as the one described above, by identifying differences between the moisture contents at each layer and determining if those differences exceed a minimum threshold. Additionally, hydrology module 144 may be configured to track theoretical minimums and maximum moisture contents for the soil and determine if any of the layers are nearing the theoretical minimums and maximums.

In an embodiment, in response to identifying a situation in which a model contains unlikely data, hydrology module 144 may create a corrected model for the field. For example, hydrology module 144 may determine the average of the water in the system and homogenize the average water over the soil profile. In the example described above where high moisture content was estimated in two layers of the soil with a low moisture content in the middle layer, hydrology module 144 would determine the average water content and apply the average to each layer of the soil, thereby resetting the system in a way that maintains the amount of water in the system without including unrealistic moisture layers.

3.5. Crop Model

Referring to FIG. 8, at step 810, a digital model of crop uptake of water is created. For example, crop module 146 may execute digitally programmed logic to model the growth of one or more crops and the uptake of water of the one or more crops during various stages of crop growth, based, at least in part, on hydrology data received from hydrology module 144, nutrient data received from fertility advisor module 136, and crop data received from field manager computing device 104. Additionally, crop module 146 may include temperature data received from temperature module 142 and soil data receive from field manager computing device 104 or external data server computer 108 in the model of the growth of the one or more crops.

Crop module 146 may determine the rate at which the one or more crops absorb the currently available water in the soil and release the available water through evapotranspiration. For example, crop module 146 may store values that indicate the rate of water uptake by crops of various types during various stages of development. Crop module 146 may identify the particular crop type from field data 106 received from field manager computing device 104 and use the water uptake rate associated with the particular crop type. For purposes of creating an estimate of nutrient availability, the absorption of water by the one or more crops may result in a lower moisture content of the soil which affects the movement of the nutrients through the soil and the loss of nutrients due to chemical interactions, such as leaching, volatilization, and denitrification. Thus, crop module 146 may send updates to hydrology module 144 to indicate the reduction of water in the soil due to water uptake by the one or more crops.

At step 812, a digital model of crop uptake of nutrients is created. For example, crop module 146 may execute digitally programmed logic to model the growth of one or more crops and the uptake of nutrients of the one or more crops during various stages of crop growth, based, at least in part, on hydrology data received from hydrology module 144, nutrient data received from fertility advisor module 136, and crop data received from field manager computing device 104. Crop module 146 may initially determine the current stage of development for the one or more crops. Additionally, crop module 146 may determine the growth in leaf area and stem weight and their current nutrient concentrations. Based on these values and on an identification of a type of crop, crop module 146 may determine one or more nutrient demands from the crop. The nutrient demands may be adjusted by the maximum accumulation of the one or more crops, available soil, and other environmental factors. In an embodiment, crop module 146 uses an estimate of currently available nutrients received from fertility advisor module 136 to fulfill the nutrient demand by the crop. Once the currently available nutrients have been used by the crop, crop module 146 may send data to fertility advisor module 136 indicating the loss of the nutrients to the soil.

In an embodiment, crop module 146 identifies days when available nutrients or available water within the soil falls short of the demand of the one or more crops. For example, crop module 146 may determine that in two months, the available nitrogen in the one or more fields will drop below the demand of the one or more crops due to a combination of nitrogen uptake, leaching, volatilization, and denitrification. In response to determining that the one or more crops will not be able to meet their nitrogen demands, crop module 146 may send data to fertility advisor module 136, recommendation module 152, presentation layer 134 and/or agronomic model module 154. Additionally, crop module 146 may update the model of the crop's development based on the lack of nitrogen and/or water. For example, a deficiency in nitrogen limits the leaf area development for a crop. Additionally, nitrogen stress may impact photosynthesis for a crop once the nitrogen concentration for the crop falls below a critical threshold. In an embodiment, crop module reduces the leaf area for the crop and the growth of the crop in the digital model of the crop based, at least in part, on determining that the a shortfall of nitrogen exists in the system.

4. Data Usage 4.1. Nutrient Availability Graphs

Figure 9:
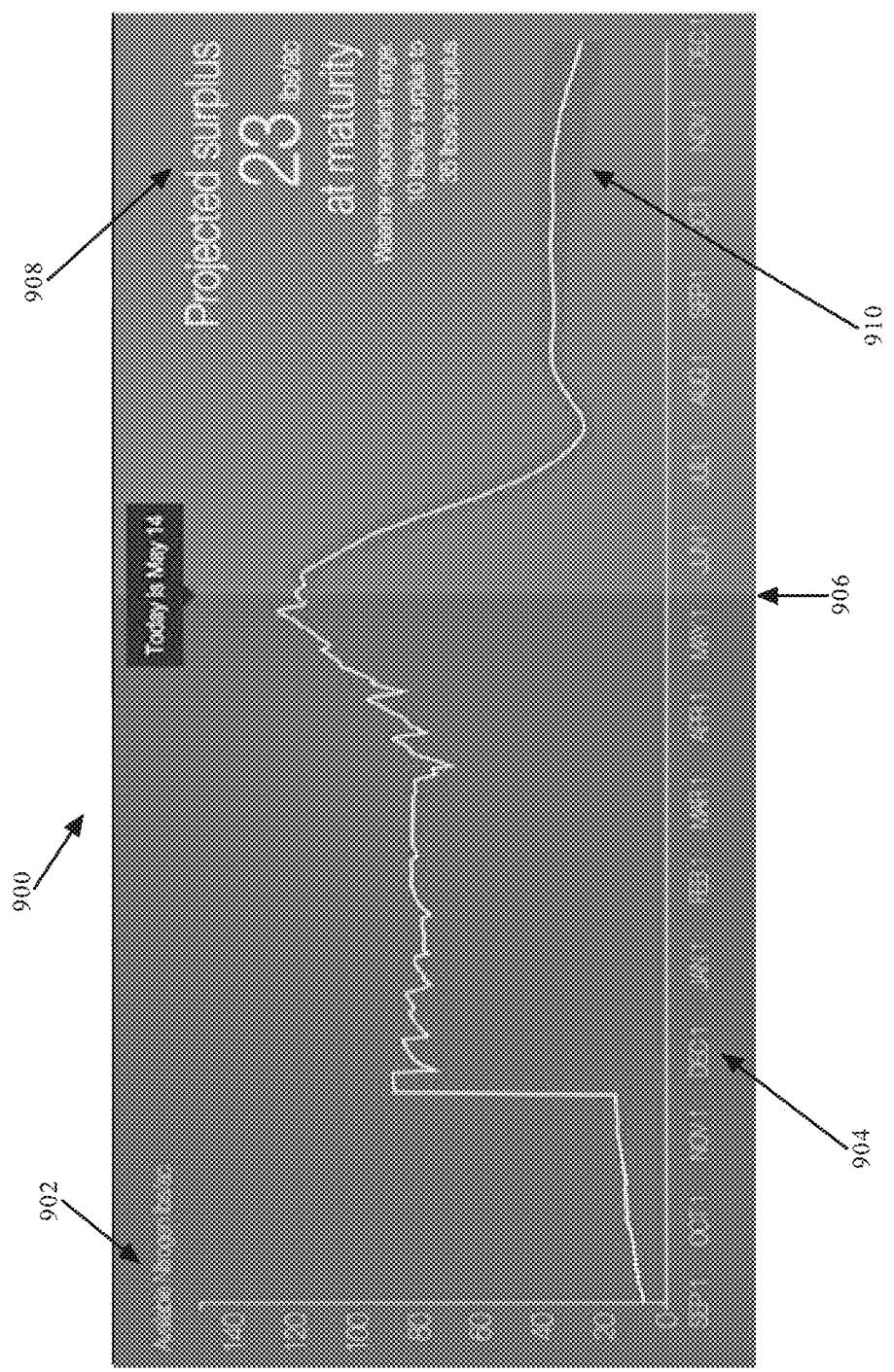
FIG. 9 depicts an example nutrient availability graph for nitrogen.

In an embodiment, nutrient display module 148 constructs one or more nutrient availability graphs from the nutrient availability data and sends the one or more nutrient availability graphs to field manager computing device 104. FIG. 9 depicts an example nutrient availability graph for nitrogen. Nutrient availability graph 900 contains nutrient axis 902, date axis 904, current date transition 906, fertility status 908, potential range 910, and event information 912. Nutrient axis 902 describes amounts of a particular nutrient that is available to the crop. For example, nutrient axis 902 in FIG. 9 contains nitrogen amounts ranging from zero pounds per acre to one hundred fifty pounds per acre. Similar availability graphs may be generated for other nutrients, such as phosphorus and potassium. Date axis 904 depicts a timeline over which nitrogen availability for the one or more crops is depicted as a function of time. For example, date axis 904 depicts data points comprising the first day of each month between September $1^{st}$ of one year and December $1^{st}$ of the next year. In an embodiment, date axis 904 is generated to correspond to the development cycle of a crop. For example, date axis 904 in FIG. 9 may correspond to a crop that was planted on or after September 1$^{st}$ and reaches maturity on or before December 1$^{st}$ of the following year. Current date transition 906 depicts a point on the graph corresponding to a current date. The portion of the graph prior to current date transition 906 depicts past amounts of a nutrient available to the crop. The portion of the graph following current date transition 906 depicts the modeled nutrient availability for the crop over a period of time between the current date and the maturity of the crop.

Fertility status 908 depicts the status of the crop with respect to the graphed nutrient. For example, fertility status 908 in FIG. 9 is depicted as a projected surplus or shortfall which indicates an amount of nitrogen available to the crop when the crop reaches maturity. In the embodiment displayed in FIG. 9, if fertility status 908 depicts a surplus, such as displayed in FIG. 9, fertility status 908 may indicate the amount of nitrogen available which exceeds the needs of the crop. If fertility status 908 indicates a shortfall, fertility status 908 may indicate an amount of nitrogen that corresponds to nitrogen needs of the crop that are not met. For example, fertility advisor module 136 may subtract the available nitrogen at maturity from the needs of the crop to determine the shortfall at maturity. While FIG. 9 depicts a projected surplus and shortfall, fertility status 908 may be a binary indicator which merely describes whether a crop's nutrient needs will be met. In an embodiment, an appearance of nutrient availability graph 900 changes depending on the availability of the nutrient at maturity. For example, if fertility status 908 depicts a surplus, the portion of nutrient graph following current date transition 906 may be displayed as green. If fertility status 908 depicts a shortfall, the portion of nutrient graph following current date transition 906 may be displayed as red. If a surplus of a nutrient available at maturity falls below a particular threshold or if the potential range of available nutrients includes both a surplus and a shortfall, the portion of nitrogen availability graph 900 following current date transition 906 may be displayed as yellow to indicate a possibility of a shortfall.

Potential range 910 depicts a potential range of nutrient availability based on uncertainties in specific estimates. For example, estimates of past precipitation may be fairly precise as they may be based on actual precipitation observations at observation posts. Estimates of precipitation in the near future may be slightly less accurate as they may be based on precipitation forecasts for generalized areas. Estimates of precipitation multiple months into the future may be even less accurate as they may be based on class averages of precipitation in the past or on precipitation trends in the past. Estimates of temperature may contain similar uncertainties. In an embodiment, fertility advisor module 136 accounts for the uncertainties by creating digital models based on the different likely precipitation and temperature scenarios. Fertility advisor module 136 may use the nutrient availability from models which estimate the lowest nitrogen availability at maturity and models which estimate the highest nutrient availability at each point to create potential range 910. For example, in FIG. 9, fertility advisor module 136 may have determined that the model depicting the lowest nitrogen availability for November 1$^{st}$ included a nitrogen availability estimate of thirty pounds per acre while the model depicting the highest nitrogen availability included a nitrogen availability estimate of forty pounds per acre. While the white line indicating the estimated nitrogen availability indicates a likely nitrogen availability of thirty five pounds per acre, the gray area which depicts potential range 910 encompasses values between thirty pounds per acre and forty pounds per acre to account for uncertainties in future weather predictions.

In an embodiment, the nutrient availability graph depicts an amount of the nutrient that is accessible to the one or more crops. For example, a user may indicate an application of sixty pounds per acre of nitrogen to one or more fields. In response, fertility advisor module 136 may store data indicating that sixty pounds of nitrogen per acre have been added to the one or more fields. Additionally, fertility advisor module 136 may determine a current availability of nitrogen to the crops using techniques described herein for determining nitrogen transmission rates based on temperature and moisture content of the soil. Nutrient display module 148 may display in the nutrient availability graph the amount of the nutrient that the crop is capable of accessing instead of displaying the amount of the nutrient that exists in the system. By displaying the amount of the nutrient the crop is capable of accessing, nutrient display module 148 provides information that would otherwise be unavailable. For example, a lab test of different layers of the soil may measure nitrogen levels within the soil, but would be unable to give an estimate of the nitrogen that is available to a crop. While the concentration of a nutrient in the soil is important, the crop is primarily affected by its ability to receive the nutrient. For example, if nitrogen is applied right before a time of shortage, a graph of nitrogen availability in the soil may show that only a small amount of the added nitrogen becomes available to the crop immediately. Thus, the field may still experience a shortfall in nitrogen which damages the crop growth even though nitrogen was added before the shortfall occurred. While a graph of nitrogen availability would show the effects of a late nitrogen application, a depiction of nitrogen in the soil would create a false illusion that the crop is always capable of receiving enough nitrogen to meet its need.

Nutrient display module 148 may additionally send event information 912 to field manager computing device 104. Event information 912 may be sent as part of nutrient availability graph 900 or sent on its own to be displayed to a user of field manager computing device 104. In an embodiment, event information 912 describes fertility information for a crop based on data received from fertility module 140, temperature module 142, hydrology module 144, and crop module 146. The fertility information may include dates and characteristics of management events such as planting, fertilizer applications, and tillage events, date ranges and amounts of nitrogen losses along with a description of the nitrogen loss, such as through volatilization, runoff, leaching, or denitrification, noteworthy patterns in chemical transformations within the soil such as soil mineraliztation, adsorption or desorption processes, and nitrification, and date ranges and severities of crop stress, such as nitrogen stress, water stress, and temperature stress. For example, event information 912 in FIG. 9 describes nitrogen application events, nitrogen loss events due to volatilization, and nitrogen loss events due to precipitation, including the dates for each event and the amount of nitrogen that was gained/loss due to the events. In an embodiment, nutrient display module 148 labels nutrient availability graph 900 with indicators for each event so that a viewer of nutrient availability graph 900 can understand a cause for each nutrient loss and gain displayed on nutrient availability graph 900.

4.2. Agronomic Models

In an embodiment, fertility advisor module 136 sends nutrient availability data to agronomic model module 154. Additionally, temperature module 142, hydrology module 144, and crop module 146 may send temperature, hydrology, and crop growth data respectively to agronomic model module 154. In an embodiment, an agronomic model is a data structure in memory of agricultural intelligence computer system 130 that contains location and crop information for one or more fields. An agronomic model may also contain agronomic factors which describe conditions which may affect the growth of one or more crops on a field. Additionally, an agronomic model may contain recommendations based on agronomic factors such as crop recommendations, watering recommendations, planting recommendations, and harvesting recommendations. The agronomic factors may also be used to estimate one or more crop related results, such as agronomic yield. The agronomic yield of a crop is an estimate of quantity of the crop that is produced, or in some examples the revenue or profit obtained from the produced crop.

Lack of one or more nutrients may affect the potential yield of a crop. For example, nitrogen stress describes the effect of a crop's inability to receive an optimal amount of nitrogen on the growth of the crop. Each crop has a different optimal amount of nitrogen which defines a minimum amount of nitrogen below which the growth of the crop is adversely affected. Optimal amounts of nitrogen may change throughout the development cycle of the crop. Water stress likewise describes the effect of a crop's inability to receive an optimal amount of water on the growth of the crop and heat stress describes the effect of high temperatures on the growth of the crop. Based on received temperature, hydrology, and nutrient data, agronomic model module 154 may estimate the effects of nitrogen stress, heat stress, and water stress on the one or more crops. For example, nitrogen stress may lead to leaf destruction which lowers the leaf area index for a crop, thereby reducing the amount of sunlight received by the crop. Agronomic model module 154 may use digitally programmed logic and stored data indicating effects of specific amounts of nitrogen stress for a particular crop type to model changes in a crop's development. Based on the models of the crop as affected by either nitrogen stress, heat stress, water stress, or any combination thereof agronomic model module 154 may estimate a total yield for the crop.

In an embodiment, agricultural intelligence computer system 130 uses the nutrient availability data, water flow data, temperature data, and crop data to create an agronomic model in memory or in persistent storage in response to a request from field manager computing device 104 for an agronomic model. In other embodiments, agricultural intelligence computer system 130 receives a request from a third party for an agronomic model. For example, an insurance company may request an agronomic model for an insured customer's field to determine the risks associated with the crop planted by the customer. In another example, an application server may send a request to agricultural intelligence computer system 130 to create an agronomic model for a specific user's field. Alternatively, agricultural intelligence computer system 130 may generate agronomic models periodically. Agricultural intelligence computer system 130 may also generate agronomic models in response to receiving updated weather observations or in response to creating updated weather data, nutrient data, soil data, or other field data.

In an embodiment, agricultural intelligence computer system 130 sends agronomic models to field manager computing device 104. In other embodiments, recommendation module 152 creates recommendations using agronomic models and sends the recommendations to field manager computing device 104. Agricultural intelligence computer system 130 may also store agronomic models in memory. Stored agronomic models may later be used to improve methods used by agronomic model module 154 or to rate the various modeling methods.

4.3. Recommendations

In an embodiment, recommendation module 152 creates one or more recommendations based on the nutrient availability data. The one or more recommendations may include current watering recommendations, current nutrient application recommendations, and enhanced efficiency agrochemical application. For example, fertility advisor module 136 may determine that nitrogen in the one or more fields will fall short of the nitrogen requirements for a crop on a certain date. In response, fertility advisor module 136 may model nitrogen applications prior to the certain date to determine when nitrogen would need to be added to the system to avoid the shortfall or to avoid the crop suffering damage from the shortfall. Recommendation module 152 may create one or more recommendations for nitrogen application based on the determination of fertility advisor module 136. Additionally, fertility advisor module 136 may determine if nitrogen lost to leaching, volatilization, or denitrification from the modeled nitrogen applications exceeds a specific threshold, and, in response to determining that the nitrogen loss exceeds the specific threshold, model applications of nitrogen inhibitors along with the nitrogen. Additionally and/or alternatively, recommendation module 152 may recommend an application of nitrogen inhibitors in response to a determination that nitrogen lost from the modeled nitrogen applications exceeds the specific threshold.

Recommendation module 152 may create a recommendation for water application based on data received from hydrology module 144 and agronomic model module 154. For example, recommendation module 152 may create a recommendation for water application in response to determining that water stress on the crop will adversely affect the agronomic yield of the crop. Water application recommendations may include specific watering dates based on temperature projections, nutrient applications, and hydrology data. For example, hydrology module 144 may model the flow of water through the soil for multiple days and determine optimal models based on the efficiency of the watering. A first model of water application may show a large percentage of the water evaporating due to high heat. A second model of water application may show a large decrease in nutrient availability due to leaching. A third model of water application may show damage to the crop based on water being applied too late. Recommendation module 152 may create a recommendation that minimizes negative effects based on the models. Additionally and/or alternatively, agronomic model module 154 may model the agronomic yield for each model. Recommendation module 152 may create a recommendation that includes parameters in the model that generated the highest agronomic yield.

Recommendation module 152 may also create recommendations for water application based on a determination of fertility advisor module 136. For example, if fertility advisor module 136 determines that low moisture content in the soil is causing less of a nutrient to be available to the crop, recommendation module 152 may create a recommendation for water application in order to increase the nutrient availability for the crop. Fertility advisor module 136 may be configured to determine whether moisture content of the soil falls below a specific threshold. In response to the determination, fertility advisor module 136 may model the effects of adding water to the soil. In an embodiment, if fertility advisor module 136 determines that the addition of water increases the nutrient availability to the soil by more than a specific threshold, recommendation module 152 may create a recommendation for an application of water.

Recommendation module 152 may also create recommendations to apply to future crops. For example, fertility advisor module 136 may create alternative models of nutrient availability based on various field conditions, such as planting dates of the crop. If the nutrient availability is higher for a crop for an earlier planting date or if applications of a nutrient are more effective for the earlier planting date, recommendation module 152 may recommend planting the next crop earlier. Recommendation module 152 may make recommendations to apply to future crops based on models of the future crop that use the output from the current crop as input data. For example, the type of crop currently in the field and the amount of a nutrient available in the field after a crop has been harvested affects the nutrient availability for the next planted crop. Fertility advisor module 136 may create models of nutrient availability for a future crop with various planting dates, nutrient application dates, and tillage methods. Fertility advisor module 136 may select a model which receives higher nutrient availability or more effective nutrient applications as an optimal model. Additionally, fertility advisor module 136 may send the nutrient data to agronomic model module 154. Agronomic model module 154 may determine a model which results in a higher yield or higher return on investment. In response, recommendation module 152 may send a recommendation for the future crop that includes parameters of the optimal model.

In an embodiment, fertility advisor module 136 sends the one or more recommendations to presentation layer 134. Presentation layer 134 may then send the one or more recommendations to field manager computing device 104. For example, field manager computing device 104 may send a request to agricultural intelligence computer system 130 for a planting recommendation for the next crop. Additionally and/or alternatively, field manager computing device 104 may send a request to agricultural intelligence system 130 for a nutrient application recommendation. In response, presentation layer 134 may send a recommendation generated by recommendation module 152 to field manager computing device 104. The recommendation may be accompanied by nutrient availability graphs that depict nutrient availability for the crop based on an application of the recommendation.

In an embodiment, recommendation module 152 sends the one or more recommendations to communication layer 132. Communication layer 132 may use the recommendations for water application, nutrient application, or enhanced efficiency agrochemical application to create application parameters for application controller 114. For example, recommendation module 152 may create a recommendation for nutrient application based on nutrient availability data received from fertility advisor module 136. In response to receiving the recommendation, communication layer 132 may use the nutrient availability data to create application parameters for a nutrient release valve that describe an amount of a nutrient to release on to the one or more fields. Presentation layer 134 may then send a notification to field manager computing device 104 indicating the nutrient availability data and requesting permission to apply the recommended nutrient to the one or more fields. In response to receiving permission to apply the recommended nutrient, communication layer 132 may send the application parameters to application controller 114. Application controller 114 may then implement the application parameters, such as releasing nitrogen onto the one or more fields or increasing the amount of water released to a specific crop.

4.4. Notifications

In an embodiment, presentation layer 134 sends notifications to field manager computing device 104. Presentation layer 134 may send notifications to field manager computing device 104 based on the one or more agronomic models, the one or more recommendations, and/or the one or more nutrient availability graphs. In an embodiment, presentation layer 134 may send a notification to field manager computing device 104 in response to determining a change in the nutrient availability for the one or more crops on the one or more fields. For example, presentation layer 134 may be programmed or configured to send a notification to field manager computing device 104 in response to determining: that the amount of available a nutrient at maturity for the crop has changed from a surplus to a shortfall or vice versa, that the shortfall of available nutrients at maturity has increased by more than a threshold value or decreased by more than a threshold value, that the surplus of available nutrients at maturity has increased by more than a threshold value or decreased by more than a threshold value, that a shortfall of nutrients has existed for longer than a threshold period of time, or that a threshold period of time has passed since a prior update.

Additionally, presentation layer 134 may send notifications to field manager computing device 104 in response to receiving one or more recommendations or detecting a change in one or more agronomic variables of the agronomic model. For example, if recommendation module 152 creates a watering recommendation based on a lack of available nutrients to the crops, presentation layer 134 may send the recommendation to field manager computing device 104. Additionally, if one of the agronomic variables, such as total yield, changes based on the nutrient availability to the crop, presentation layer 134 may send a notification to field manager computing device 104 indicating that the change in the agronomic variable. For example, agronomic model module 154 may recalculate the total yield for the crop based on the nutrients available to the crop. If agronomic model module 154 determines that the yield has decreased due to low nutrient availability, presentation layer 134 may send a notification to field manager computing device 104 indicating that the total yield has decreased. In an embodiment, the recommendations may be sent along with the notification indicating a change in the agronomic variable. For example, a recommendation to increase the amount of water received by the crop may be accompanied with an indication that the projected total yield for the crop has decreased based on lack of moisture.

In an embodiment, presentation layer 134 sends the one or more nutrient graphs, the recommendations, the agronomic models, and/or other field information to field manager computing device 104 in response to receiving a request from field manager computing device 104. For example, field manager computing device 104 may send a message directly to agricultural intelligence computer system 130 or to an application server through an application executing on field manager computing device 104 requesting information about the one or more fields. In response, presentation layer 134 may cause display of a graphical user interface on field manager computing device 104 that includes the one or more nutrient graphs, the recommendations, one or more agronomic variables such as growing degree days or total crop yield, and/or other field information such as the crop type or tillage methods used on the crop. In an embodiment, the request for information from agricultural intelligence computing system is generated in a notification sent by presentation layer 134. For example, presentation layer 134 may send a notification to field manager computing device 104 indicating low nutrient availability in the field. Upon receiving a selection of the notification, field manager computing device 104 may send a message to agricultural intelligence computer system 130 requesting the additional information. Additionally, a selection of the notification may cause an application to execute on field manager computing device 104 through which agricultural intelligence computer system 130 may cause display of the additional information.

4.5. User Defined Proposals

In an embodiment, nutrient availability is determined by fertility advisor module 136 in response to receiving data from field manager computing device 104 indicating an application of a nutrient on the one or more fields. For example, presentation layer 134 may cause display on field manager computing device 104 of a user interface for indicating an application of a particular nutrient. The interface may include a date for the nutrient application. In response to receiving input identifying an amount of a nutrient, a type of nutrient, and a date of application, field manager computing device 104 may send a message to agricultural intelligence computer system 130 indicating the application of the nutrient. Based on the nutrient application data, field data 106, external data 110, temperature data received from temperature module 142, hydrology data received from hydrology module 144, and crop data received from crop module 146, fertility advisor module 136 may determine an overall effect of the nutrient application. For example, fertility advisor module 136 may identify the available nutrients in the system over the course of development of the crop based on the proposed nutrient application. Fertility advisor module 136 may create a digital model of the availability of a nutrient as described herein with the additional nutrients, applied on the proposed date, modeled into the system. Additionally, fertility advisor module 136 may identify available nutrients in the system based on data indicating multiple applications of the nutrient. For example, fertility advisor module 136 may create a digital model of the availability of nitrogen as described herein with the additional nitrogen applied on multiple dates modeled into the system.

In an embodiment, presentation layer 134 also causes display through the user interface of field manager computing device 104 of controls for indicating an application of one or more enhanced efficiency agrochemicals, such as nitrapyrin, along with the application of the nutrient. In response to receiving an indication of an application of enhanced efficiency agrochemicals, fertility advisor module 136 may create a model that includes the application of nutrient along with the enhanced efficiency agrochemicals. In some embodiments, in response to receiving a proposal for an application of a nutrient, fertility advisor module 136 may create a model based on the proposal without the application of the enhanced efficiency agrochemicals and a model based on the proposal with the application of the enhanced efficiency agrochemicals. Presentation layer 134 may send the available nutrient results to field manager computing device 104 in order to allow a comparison of nutrient availability based on the application or absence of the enhanced efficiency agrochemicals. In this manner, agricultural intelligence computer system 130 creates a means for a user to evaluate the benefits of using enhanced efficiency agrochemicals, such as nitrogen inhibitors.

By estimating the amount of a nutrient available to the system over the course of development of a crop along based, in part, on proposed nutrient applications, agricultural intelligence computer system 130 creates a means for a user to effectively plan nutrient application into a field. For example, a user may input a plurality of proposed nitrogen applications before a crop's development or evenly spaced throughout a crop's development. While nitrogen is applied uniformly, the estimated heat during a specific month may lead to the applied nitrogen being volatilized more quickly, thereby reducing the amount of nitrogen available in the system. Presentation layer 134 may cause display of the nitrogen loss from the proposed application of nitrogen on field manager computing device 104. In response, the user may add a nitrogen application in close proximity to the proposed application or move the proposed nitrogen application to a colder day. Fertility advisor module 136 may then re-estimate the nitrogen available to the crop over the crop's development based on the added or changed application data. In this manner, agricultural intelligence computing system provides feedback on the effects of each nutrient application to field manager computing device 104.

In an embodiment, nutrient availability is determined by fertility advisor module 136 in response to receiving data from field manager computing device 104 indicating crop planting proposals. For example, mobile device interface module 132 may cause display of a user interface on field manager computing device 104 for inputting proposal data. Proposal data may include proposed crop type, proposed tillage method, proposed planting date, proposed irrigation, and proposed nutrient and enhanced efficiency agrochemical applications. In response to receiving crop planting proposals, fertility advisor module 136 may create one or more digital models of nutrient availability constrained by input parameters. Additionally, fertility advisor module 136 may create nutrient availability models with varying parameters. For example, fertility advisor module 136 may create models with different tillage methods and send the different nutrient availabilities to field manager computing device 104, thereby allowing a user to compare the effects on nutrient availability of different tillage methods.

In an embodiment, the user interface includes controls for setting one or more free parameters. A free parameter may be a parameter that is either not identified or is not required by the user. For example, if a user is determined to grow corn, the user may not list corn as a free parameter. If the user plans to plant the crop sometime between January and June, the user may set the date as a free parameter. In response to identifying a free parameter, fertility advisor module 136 may create multiple models of nutrient availability using different inputs for the free parameter. In an embodiment, fertility advisor module 132 selects optimal parameters based on nutrient availability through the crop development in each model. For example, if one model which includes a planting date in February contains a surplus in nitrogen availability at maturity while a model which includes a planting date in April contains a shortfall in nitrogen availability at maturity, fertility advisor module 132 may select the planting date in February as an optimal planting date over the planting date in April.

In an embodiment, nutrient display module 148 creates a nutrient graph for each proposed application of a nutrient received from field manager computing device 104. For example, agricultural intelligence computing system 120 may receive a first proposal of nitrogen application on a first date and a second proposal of nitrogen application at a second date. Nutrient display module 148 may create a first nitrogen graph including the first proposed application of nitrogen and a second nitrogen graph including the second proposed application of nitrogen. Presentation layer 134 may then send the two nitrogen graphs to field manager computing device 104, thereby allowing user 102 to compare the effects of the first proposed application of nitrogen with the affects of the second proposed application of nitrogen. Nutrient display module 148 may also create graphs of nutrient availability for different planting parameters received from field manager computing device 104. For example, if agricultural intelligence computing system 120 receives a proposal for planting a crop in February and a second proposal for planting the crop in April, nutrient display module 148 may create a nitrogen graph based on a nitrogen availability model for each planting date. Additionally, if agricultural intelligence computing system 120 receives a proposal that includes one or more free parameters, nutrient display module 148 may create a graph of nutrient availability based on digital models created with different parameters for the free parameters. For example, if planting date is set as a free parameter, fertility advisor module 136 may create a first nutrient availability graph with the planting date set in January, a second nutrient availability graph with the planting date set in February, and so on.

In an embodiment, recommendation module 152 creates one or more nutrient application recommendations based on a proposed application of a nutrient on field manager computing device 104. For example, agricultural intelligence computer system 130 may receive a proposal from field manager computing device 104 for an application of nitrogen. Fertility advisor module 136 may model flow of nitrogen through the soil using the techniques described above based on applications of nitrogen at different dates and times. In an embodiment, fertility advisor module 136 initially determines a date or time at which a shortfall would occur without a nutrient application. Fertility advisor module 136 may then model the nutrient availability based on an application of nutrient on each prior date. Based on the models of the nutrient, fertility advisor module 136 may identify an optimal timeframe in which to apply the nutrient. For example, fertility advisor module 136 may initially determine that the nitrogen availability in the one or more fields will reach a shortfall in one month. Fertility advisor module 136 may then generate different models of nitrogen availability based on nitrogen application for each day over the next month. Fertility advisor module 136 may determine that an optimal model of the models of nitrogen availability includes a higher amount of nitrogen availability at maturity than the other models, thereby indicating that less of the nitrogen is lost through leaching, volatilization, or denitrification. Based on the determination, recommendation module 152 may recommend application of nitrogen on the day or time which served as a basis for the optimal model.

In some embodiments, recommendation module 152 also generates a recommendation for an optimal amount of nutrient application based on the proposed application of the nutrient. For example, fertility advisor module 136 may initially identify the optimal time or day for a nitrogen application based on an application of a specific amount of nitrogen. Once a specific time or date is identified, fertility advisor module 136 may model the nutrient availability in the field based on different amounts of application of the nutrient. Based on the nutrient availability models, fertility advisor module 136 may determine an optimal amount of the nutrient to apply to the one or more fields. For example, a first model of nitrogen availability may indicate that twenty five percent of the nitrogen applied to the field is eventually lost to leaching, volatilization, or denitrification. A second model of nitrogen availability based on an application of a larger amount of nitrogen may indicate that more nitrogen is available to the one or more crops, but that forty five percent of the nitrogen applied to the field is lost. Based on the two models, recommendation module 152 may recommend an application of the smaller amount of nitrogen in order to increase the value of the nitrogen application. Additionally, recommendation module 152 may determine an optimal spread of nutrient applications for optimal effect. For example, if a third model of nitrogen availability based on a second application of nitrogen two weeks after the first application of nitrogen indicates that only thirty five percent of the applied nitrogen is lost, recommendation module 152 may recommend applying the optimal amount of nitrogen for the first application and applying an amount of nitrogen corresponding to the difference between the larger amount of nitrogen and the optimal amount of nitrogen during a second application of nitrogen two weeks after the first application of nitrogen.

Recommendation module 152 may be further programmed or configured to create recommendations for one or more other parameters, such as application of enhanced efficiency agrochemicals, planting date, harvest date, irrigation dates, tillage methods, and other crop related parameters. For example, if agricultural intelligence computer system 130 receives a proposal for planting a particular type of crop, fertility advisor module 136 may create digital models of nutrient availability using as input various planting dates, tillage methods, and nutrient application dates and amounts. Fertility advisor module 136 may then select an optimal model which includes the least amount of nutrient expenditure to receive a surplus. Additionally and/or alternatively, fertility advisor module 136 may select an optimal model which includes the least amount of nutrient expenditure which receives the comparatively largest surplus. For example, if an application of sixty pounds of nitrogen per acre for a first set of parameters returns a surplus of twenty pounds of nitrogen per acre and an application of one hundred pounds of nitrogen for a second set of parameters returns a surplus of twenty five pounds of nitrogen, fertility advisor module 136 may select the first set of parameters as optimal parameters because it results in the most efficient application of nitrogen.

5. Benefits of Certain Embodiments

Using the techniques described herein, a computer can deliver nutrient availability data that would be otherwise unavailable. For example, the techniques herein can determine a portion of the nitrogen within the soil of a field that is usable by the crops in the field. The performance of the agricultural intelligence computing system is improved using the techniques described herein which create accurate models with high computational efficiency, thereby reducing the amount of memory used to model future nutrient availability for a crop. Additionally, the techniques described herein may be used to create application parameters for an application controller, thereby improving the performance of farming implements controlled by the application controller.

6. Extensions and Alternatives

In the foregoing specification, embodiments have been described with reference to numerous specific details that may vary from implementation to implementation. The specification and drawings are, accordingly, to be regarded in an illustrative rather than a restrictive sense. The sole and exclusive indicator of the scope of the disclosure, and what is intended by the applicants to be the scope of the disclosure, is the literal and equivalent scope of the set of claims that issue from this application, in the specific form in which such claims issue, including any subsequent correction.

What is claimed is:

1. A method comprising:

receiving over a network at an agricultural intelligence computing system comprising one or more processors and digital memory, electronic digital data comprising a plurality of values representing crop data, soil data, and weather data for one or more fields;

using digitally programmed logic in a temperature module of the agricultural intelligence computing system, creating and storing in computer memory a first digital model of temperature of soil in the one or more fields over a particular period of time based, at least in part, on the plurality of values representing crop data, soil data, and weather data;

using digitally programmed logic in a hydrology module of the agricultural intelligence computing system, creating and storing in the computer memory a second digital model of water flow through the one or more fields over the particular period of time based, at least in part, on the plurality of values representing crop data, soil data, and weather data;

using digitally programmed logic in a crop module of the agricultural intelligence computing system, creating and storing a third digital model of an uptake of water of one or more crops on the one or more fields over the particular period of time based, at least in part, on the modeled water flow through the one or more fields and the plurality of values representing crop data, soil data, and weather data;

using digitally programmed logic in the crop module of the agricultural intelligence computing system, creating and storing a fourth digital model of an uptake of a nutrient of the one or more crops on the one or more fields over the particular period of time based, at least in part, on the plurality of values representing crop data, soil data, and weather data;

using digitally programmed logic in a fertility advisor module of the agricultural intelligence computing system, creating a fifth digital model of nutrient availability in the one or more fields over the particular period of time based, at least in part on the first digital model of temperature of soil, the second digital model of water flow, the third digital model of the uptake of water of the one or more crops, the fourth digital model of the uptake of the nutrient of the one or more crops, and the plurality of values representing crop data, soil data, and weather data for the one or more fields by:

computing an initial nutrient availability at an initial point in time comprising a portion of the nutrients in the soil that the crop is capable of accessing over the particular period of time as a function of initial nutrient levels in the soil, initial soil composition, and initial soil moisture;

computing uptake of the nutrient by the one or more crops over the particular period of time;

computing nutrient loss over the particular period of time to the atmosphere;

computing nutrient loss over the particular period of time through leaching;

for a particular point in time in the particular period of time, modeling an amount of the nutrient in the soil that the crop is capable of accessing and utilizing as the initial nutrient availability minus nutrient loss between the initial point in time and the particular point in time and nutrient loss to the atmosphere and through leaching before the uptake of the nutrient by the one or more crops over the particular period of time after the particular point in time;

using a mobile device interface module, based, at least in part, on the fifth digital model of nutrient availability, causing display on a field manager computing device of a nutrient availability graph which indicates at least:

a current modeled nutrient availability for the one or more crops of the one or more fields computed from the fifth digital model of nutrient availability; and a modeled projected future nutrient availability for the one or more crops computed from the fifth digital model of nutrient availability.

2. The method of claim 1 wherein the hydrology module creating and storing the second digital model of water flow through the one or more fields includes, for each given time step of a plurality of time steps comprises:

creating an initial estimation of water flow into the one or more fields based, at least in part, on a plurality of values representing moisture content in the one or more fields;

updating the plurality of values representing moisture content in the one or more fields.

3. The method of claim 2 wherein the hydrology module dynamically alters a size of each time step of the plurality of time steps based, at least in part, on one or more of moisture content, hydrologic gradient, or soil type of the one or more fields.

4. The method of claim 1 wherein the hydrology module creating and storing the second digital model of water flow through the one or more fields includes determining one or more shape parameters for a hydrology curve by creating a plurality of curves that fit known parameters and selecting a particular parameter for the hydrology curve that minimizes a sum of square differences between a wilting point of the hydrology curve and a field capacity of the hydrology curve.

5. The method of claim 1 further comprising:

the hydrology module, using digitally programmed logic, determining that the second digital model of water flow through the one or more fields contains one or more unrealistic moisture profiles;

the hydrology module, based on the determining, homogenizing moisture content over a soil profile of the one or more fields.

6. The method of claim 1 further comprising:

the hydrology module creating one or more watering recommendations based, at least in part, on the second digital model of water flow through the one or more fields and the plurality of values representing crop data, soil data, and weather data for one or more fields;

using a mobile device interface module, sending the one or more watering recommendations to a field manager computing device.

7. The method of claim 1 further comprising:

using the hydrology module, creating one or more watering recommendations for an application module of the agricultural intelligence computing system;

using the application module, generating instructions for an application controller based on the one or more watering recommendations and sending the instructions to the application controller;

wherein the instructions cause the application controller to control an operating parameter of an agricultural vehicle to implement the one or more watering recommendations.

8. The method of claim 1:
wherein the plurality of values representing crop data, soil data, and weather data for one or more fields include input data received from a field manager computing device comprising crop type, soil type, soil composition, and tillage methods applied to the one or more fields;
wherein the fertility advisor module of the agricultural intelligence computing system creating and displaying the fifth digital model of nutrient availability includes:
determining an effect on nutrient availability in soil of the one or more fields from the soil composition; and
determining an effect on nutrient availability in the soil of the one or more fields from the tillage methods applied to the one or more fields.

9. The method of claim 1 further comprising:
using the fertility advisor module, creating one or more stabilizer recommendations based, at least in part, on the fifth digital model of nutrient availability in the one or more fields and the plurality of values representing crop data, soil data, and weather data for one or more fields;
using a mobile device interface module, sending the one or more stabilizer recommendations to a field manager computing device.

10. The method of claim 1 further comprising:
using the fertility advisor module, creating one or more nutrient recommendations for an application module of the agricultural intelligence computing system;
using the application module, generating instructions for an application controller based on the one or more nutrient recommendations and sending the instructions to the application controller;
wherein the instructions cause the application controller to control an operating parameter of an agricultural vehicle to implement the one or more nutrient recommendations.

11. The method of claim 1 further comprising:
using the digitally programmed logic in the crop module of the agricultural intelligence computing system, determining an optimal amount of a nutrient for one or more crops associated with the plurality of values representing crop data;
determining, based on the fifth digital model of nutrient availability in the one or more fields, that a modeled amount of nutrient availability in the one or more fields is less than the optimal amount of the nutrient for the one or more crops;
using a mobile device interface module, sending a notification to a field manager computing device indicating that the modeled amount of nutrient availability in the one or more fields is less than the optimal amount of the nutrient for the one or more crops.

12. The method of claim 1 further comprising:
using a mobile device interface module, causing display on a field manager computing device of event information which includes, for a particular event:
a date of the particular event which affects the nutrient available to the one or more crops;
a description of the particular event which affects the nutrient available to the one or more crops; and
an indication of a magnitude of an effect on the nutrient available to the one or more crops from the particular event.

13. The method of claim 1, further comprising:
sending, over a network to a field manager computing device from the agricultural intelligence computing system, nutrient availability data indicating an availability of the nutrient in the one or more fields over a course of development of the one or more crops based on the fifth digital model of nutrient availability in the one or more fields;
receiving, over a network at the agricultural intelligence computing system from the field manager computing device, electronic digital data indicating a proposed application of the nutrient to the one or more fields;
using the digitally programmed logic in the fertility advisor module of the agricultural intelligence computing system, updating the fifth model of nutrient availability to include the proposed application of the nutrient to the one or more fields;
sending, over the network to the field manager computing device from the agricultural intelligence computing system, updated nutrient availability data indicating an updated availability of the nutrient in the one or more fields over the course of development of the one or more crops based on the updated fifth digital model of nutrient availability in the one or more fields.

14. The method claim 13:
wherein updating the fifth model of nutrient availability to include the proposed application of the nutrient to the one or more fields comprises:
generating a first updated model of nutrient availability with the proposed application of the nutrient, using a first set of specific parameters;
generating one or more second updated models of nutrient availability, using one or more second sets of specific parameters;
wherein each set of the one or more second sets of specific parameters includes at least one parameter that is different than a corresponding parameter in the first set of specific parameters;
determining that the first updated model of nutrient availability is an optimal model of nutrient availability;
wherein sending the updated nutrient availability data to the field manager computing device comprises:
sending nutrient availability data based on the first updated model of nutrient availability along with the first set of specific parameters.

15. The method of claim 14 wherein the first set of specific parameters includes an amount of the nutrient applied, a date of nutrient application, and an amount of an enhanced efficiency agrochemical applied.

16. A data processing system comprising:
a memory;
one or more processors coupled to the memory;
a mobile device interface module stored in the memory, executed by the one or more processors, and configured to cause the one or more processors to receive, from a field manager computing device, a plurality of values representing crop data and soil data for one or more fields;
a temperature module stored in the memory, executed by the one or more processors, and configured to cause the one or more processors to create and store in the memory a first digital model of temperature of soil in the one or more fields over a particular period of time based, at least in part, on the plurality of values representing crop data and soil data for the one or more fields;
a hydrology module stored in the memory, executed by the one or more processors, and configured to cause the one or more processors to create and store in the memory a second digital model of water flow through the one or more fields over the particular period of time based, at least in part, on the plurality of values representing crop data and soil data for the one or more fields;
a crop module stored in the memory, executed by the one or more processors, and configured to cause the one or more processors to create and store in the memory a third digital model of an uptake of water of one or more crops on the one or more fields over the particular period of time and a fourth digital model of an uptake of a nutrient of the one or more crops on the one or more fields over the particular period of time based, at least in part, on the modeled water flow through the one or more fields and the plurality of values representing crop data and soil data for the one or more fields;
a fertility advisor module stored in the memory, executed by the one or more processors, and configured to cause the one or more processors to create a fifth digital model of nutrient availability of the one or more fields over the particular period of time based, at least in part on the first digital model of temperature of soil, the second digital model of water flow, the third digital model of the uptake of water of the one or more crops, the fourth digital model of the uptake of the nutrient of the one or more crops, and the plurality of values representing crop data and soil data for the one or more fields by:
    computing an initial nutrient availability at an initial point in time comprising a portion of the nutrients in the soil that the crop is capable of accessing over the particular period of time as a function of initial nutrient levels in the soil, initial soil composition, and initial soil moisture;
    computing uptake of the nutrient by the one or more crops over the particular period of time;
    computing nutrient loss over the particular period of time to the atmosphere;
    computing nutrient loss over the particular period of time through leaching;
    for a particular point in time in the particular period of time, modeling an amount of the nutrient in the soil that the crop is capable of accessing and utilizing as the initial nutrient availability minus nutrient loss between the initial point in time and the particular point in time and nutrient loss to the atmosphere and through leaching before the uptake of the nutrient by the one or more crops over the particular period of time after the particular point in time;
wherein the mobile device interface module is further configured to, based, at least in part, on the fifth digital model of nutrient availability, cause the one or more processors to cause display on the field manager computing device of a nutrient availability graph which indicates at least:
a current modeled nutrient availability for the one or more crops of the one or more fields computed from the fifth digital model of nutrient availability; and
a modeled projected future nutrient availability for the one or more crops computed from the fifth digital model of nutrient availability.

17. The data processing system of claim 16, wherein the hydrology module is further configured to cause the one or more processors to:
    create and store in memory the second digital model of water flow through the one or more fields by, for each given time step of a plurality of time steps:
    creating an initial estimation of water flow into the one or more fields based, at least in part, on a plurality of values representing moisture content in the one or more fields;
    updating the plurality of values representing moisture content in the one or more fields;
    dynamically alter a size of each time step of the plurality of time steps based, at least in part, on one or more of moisture content, hydrologic gradient, or soil type of the one or more fields.

18. The data processing system of claim 16 wherein the hydrology module is further configured to cause the one or more processors to create and store in memory the second digital model of water flow through the one or more fields by determining one or more shape parameters for a hydrology curve by creating a plurality of curves that fit known parameters and selecting a particular parameter for the hydrology curve that minimizes a sum of square differences between a wilting point of the hydrology curve and a field capacity of the hydrology curve.

19. The data processing system of claim 16:
    wherein the hydrology module is further configured to cause the one or more processors to create and store the second digital model of water flow through the one or more fields by:
    determining that the second digital model of water flow through the one or more fields contains one or more unrealistic moisture profiles;
    based on the determining, homogenizing moisture content over a soil profile of the one or more fields.

20. The data processing system of claim 16:
    wherein the hydrology module is further configured to cause the one or more processors to create and store in memory one or more watering recommendations based, at least in part, on the second digital model of water flow through the one or more fields and the plurality of values representing crop data and soil data for the one or more fields, the system further comprising:
    wherein the mobile device interface module is further configured to cause the one or more processors to send the one or more watering recommendations to the field manager computing device.

21. The data processing system of claim 16, wherein the hydrology module is further configured to cause the one or more processors to create and store in memory one or more watering recommendations based, at least in part, on the second digital model of water flow through the one or more fields and the plurality of values representing crop data and soil data for the one or more fields, the system further comprising:
    an application module stored in the memory, executed by the one or more processors, and configured to cause the one or more processors to generate instructions for an application controller based on the one or more watering recommendations and send the instructions to the application controller;
    wherein the instructions cause the application controller to control an operating parameter of an agricultural vehicle to implement the one or more watering recommendations.

22. The data processing system of claim 16:
wherein the plurality of values representing crop data and soil data for the one or more fields include input data received from the field manager computing device comprising crop type, soil type, soil composition, and tillage methods applied to the one or more fields;
wherein the fertility advisor module is further configured to cause the one or more processors to create and display the fifth digital model of nutrient availability of the one or more fields by:
determining an effect on nutrient availability in soil of the one or more fields from the soil composition; and
determining an effect on nutrient availability in the soil of the one or more fields from the tillage methods applied to the one or more fields.

23. The data processing system of claim 16:
wherein the fertility advisor module is further configured to cause the one or more processors to create and store in the memory one or more stabilizer recommendations based, at least in part, on the fifth digital model of nutrient availability in the one or more fields and the plurality of values representing crop data and soil data;
wherein the mobile device interface module is further configured to cause the one or more processors to send the one or more stabilizer recommendations to the field manager computing device.

24. The data processing system of claim 16 wherein the fertility advisor module is further configured to cause the one or more processors to create and store in the memory one or more nutrient recommendations based, at least in part, on the fifth digital model of nutrient availability in the one or more fields and the plurality of values representing crop data and soil data, the system further comprising:
an application module, stored in the memory, executed by the one or more processors, and configured to cause the one or more processors to generate instructions for an application controller based on the one or more nutrient recommendations and send the instructions to the application controller;
wherein the instructions cause the application controller to control an operating parameter of an agricultural vehicle to implement the one or more nutrient recommendations.

25. The data processing system of claim 16:
wherein the crop module is further configured to cause the one or more processors to determine an optimal amount of the nutrient for the one or more crops associated with the plurality of values representing crop data;
wherein the crop module is further configured to cause the one or more processors to determine, based on the fifth digital model of nutrient availability in the one or more fields, that a modeled amount of nutrient availability in the one or more fields is less than the optimal amount of the nutrient for the one or more crops;
wherein the mobile device interface module is further configured to cause the one or more processors to send a notification to the field manager computing device indicating that the modeled amount of nutrient availability in the one or more fields is less than the optimal amount of the nutrient for the one or more crops.

26. The data processing system of claim 16:
wherein the mobile device interface module is further configured to cause the one or more processors to cause display on the field manager computing device of event information which includes, for a particular event:
a date of the particular event which affects the nutrient available to the one or more crops;
a description of the particular event which affects the nutrient available to the one or more crops; and
an indication of a magnitude of an effect on the nutrient available to the one or more crops from the particular event.

27. The data processing system of claim 16:
wherein the mobile device interface module is further configured to cause the one or more processors to send to the field manager computing device nutrient availability data indicating an availability of the nutrient in the one or more fields over a course of development of the one or more crops based on the fifth digital model of nutrient availability in the one or more fields;
wherein the mobile device interface module is further configured to cause the one or more processors to receive from the field manager computing device electronic digital data indicating a proposed application of the nutrient to the one or more fields;
wherein the fertility advisor module is further configured to cause the one or more processors to update the fifth digital model of nutrient availability to include the proposed application of the nutrient to the one or more fields;
wherein the mobile device interface module is further configured to cause the one or more processors to send to the field manager computing device updated nutrient availability data indicating an updated availability of the nutrient in the one or more fields over the course of development of the one or more crops based on the updated fifth digital model of nutrient availability in the one or more fields.

28. The data processing system of claim 27:
wherein the fertility advisor module is further configured to cause the one or more processors to update the fifth digital model of nutrient availability to include the proposed application of the nutrient to the one or more fields by:
generating a first updated model of nutrient availability with the proposed application of the nutrient, using a first set of specific parameters;
wherein the first set of specific parameters includes an amount of the nutrient applied, a date of nutrient application, and an amount of enhanced efficiency agrochemicals applied;
generating one or more second updated models of nutrient availability, using one or more second sets of specific parameters;
wherein each set of the one or more second sets of specific parameters includes at least one parameter that is different than a corresponding parameter in the first set of specific parameters;
determining that the first updated model of nutrient availability is an optimal model of nutrient availability;
wherein the mobile device interface module is further configured to cause the one or more processors to send to the field manager computing device updated nutrient availability data indicating an updated availability of the nutrient in the one or more fields over the course of development of the one or more crops by:
sending nutrient availability data based on the first updated model of nutrient availability along with the first set of specific parameters.

* * * * *